(12) United States Patent
Tate

(10) Patent No.: US 9,932,385 B2
(45) Date of Patent: Apr. 3, 2018

(54) MUTANT PROTEINS AND METHODS FOR THEIR PRODUCTION

(71) Applicant: Medical Research Council, Swindon (GB)

(72) Inventor: Christopher Gordon Tate, Cambridge (GB)

(73) Assignee: Medical Research Council, Swindon (GB)

( * ) Notice: Subject to any disclaimer, the term of this patent is extended or adjusted under 35 U.S.C. 154(b) by 0 days.

(21) Appl. No.: 14/776,908

(22) PCT Filed: Mar. 13, 2014

(86) PCT No.: PCT/GB2014/050757
§ 371 (c)(1),
(2) Date: Sep. 15, 2015

(87) PCT Pub. No.: WO2014/140586
PCT Pub. Date: Sep. 18, 2014

(65) Prior Publication Data
US 2016/0031966 A1 Feb. 4, 2016

Related U.S. Application Data

(60) Provisional application No. 61/790,592, filed on Mar. 15, 2013.

(51) Int. Cl.
*C07K 14/705* (2006.01)
*G01N 33/68* (2006.01)

(52) U.S. Cl.
CPC ....... *C07K 14/70571* (2013.01); *G01N 33/68* (2013.01)

(58) Field of Classification Search
None
See application file for complete search history.

(56) References Cited

FOREIGN PATENT DOCUMENTS

| WO | WO 1993/08261 A1 | 4/1993 |
|---|---|---|
| WO | WO 2008/004223 A2 | 1/2008 |
| WO | WO 2008/114020 A2 | 9/2008 |
| WO | WO 2009/071914 A2 | 6/2009 |

OTHER PUBLICATIONS

Genbank Accession No. AAR34663. Aug. 20, 1993. Rat 5HT transporter.
Abdul-Hussein et al., Thermostabilisation of the serotonin transporter in a cocaine-bound conformation. J Mol Biol. Jun. 26, 2013;425(12):2198-207. doi: 10.1016/j.jmb.2013.03.025.
Abramson et al., Structure and mechanism of the lactose permease of *Escherichia coli*. Science. Aug. 1, 2003;301(5633):610-5.
Bill et al., Overcoming barriers to membrane protein structure determination. Nat Biotechnol. Apr. 2011;29(4):335-40. doi: 10.1038/nbt.1833.
Bröer et al., The solute carrier 6 family of transporters. Br J Pharmacol. Sep. 2012;167(2):256-78. doi: 10.1111/j.1476-5381.2012.01975.x.
Chen et al., Structure and function of the dopamine transporter. Eur J Pharmacol. Sep. 29, 2000;405(1-3):329-39.
Cherezov et al., High-resolution crystal structure of an engineered human beta2-adrenergic G protein-coupled receptor. Science. Nov. 23, 2007;318(5854):1258-65. Epub Oct. 25, 2007.
Grisshammer et al., Overexpression of integral membrane proteins for structural studies. Q Rev Biophys. Aug. 1995;28(3):315-422.
Hahn et al., The functional impact of SLC6 transporter genetic variation. Annu Rev Pharmacol Toxicol. 2007;47:401-41.
Hino et al., G-protein-coupled receptor inactivation by an allosteric inverse-agonist antibody. Nature. Jan. 29, 2012;482(7384):237-40. doi:10.1038/nature10750. Supplementary Information.
Jardetzky, Simple allosteric model for membrane pumps. Nature. Aug. 27, 1966;211(5052):969-70.
Kristensen et al., SLC6 neurotransmitter transporters: structure, function, and regulation. Pharmacol Rev. Sep. 2011;63(3):585-640. doi:10.1124/pr.108.000869. Epub Jul. 13, 2011.
Lebon et al., Agonist-bound adenosine A(2A) receptor structures reveal common features of GPCR activation. Nature. May 18, 2011;474(7352):521-5. doi: 10.1038/nature10136. Supplementary Information.
Lebon et al., Thermostabilisation of an agonist-bound conformation of the human adenosine A(2A) receptor. J Mol Biol. Jun. 10, 2011;409(3):298-310. doi: 10.1016/j.jmb.2011.03.075. Epub Apr. 9, 2011.
Magnani et al., Co-evolving stability and conformational homogeneity of the human adenosine A(2a) receptor. Proc Natl Acad Sci U S A. Aug. 5, 2008;105(31):10744-9. doi:10.1073/pnas.0804396105. Epub Jul. 29, 2008. Supporting Information.
Magnani et al., Partitioning of the serotonin transporter into lipid microdomains modulates transport of serotonin. J Biol Chem. Sep. 10, 2004;279(37):38770-8. Epub Jun. 29, 2004.
Miller et al., Engineering an ultra-thermostable β(1)-adrenoceptor. J Mol Biol. Oct. 28, 2011;413(3):628-38. doi: 10.1016/j.jmb.2011.08.057. Epub Sep. 6, 2011.
Rasmussen et al., Biophysical characterization of the cocaine binding pocket in the serotonin transporter using a fluorescent cocaine analogue as a molecular reporter. J Biol Chem. Feb. 16, 2001;276(7):4717-23. Epub Nov. 2, 2000.
Rasmussen et al., Crystal structure of the human beta(2) adrenergic G-protein-coupled receptor. Nature. Nov. 15, 2007;450(7168):383-7. Epub Oct. 21, 2007.

(Continued)

*Primary Examiner* — John D Ulm
(74) *Attorney, Agent, or Firm* — Wolf, Greenfield & Sacks, P.C.

(57) ABSTRACT

The present invention relates to mutant transmembrane proteins which have increased conformational stability when compared to their parent protein, methods of selection and production. In particular the invention relates to mutant transmembrane proteins which are mutated in or in the proximity of the transmembrane alpha helices or in a kinked region or in an alpha-helix adjacent to a kink. The mutant transmembrane proteins have use in crystallization studies and also in screening to identify compounds for use in drug discovery and therapy.

8 Claims, 14 Drawing Sheets

(56) References Cited

OTHER PUBLICATIONS

Rasmussen et al., Structure of a nanobody-stabilized active state of the β(2) adrenoceptor. Nature. Jan. 13, 2011;469(7329):175-80. doi: 10.1038/nature09648.

Rosenbaum et al., GPCR engineering yields high-resolution structural insights into beta(2)-adrenergic receptor function. Science. Nov. 23, 2007;318(5854):1266-73. Epub Oct. 25, 2007.

Sarker et al., The high-affinity binding site for tricyclic antidepressants resides in the outer vestibule of the serotonin transporter. Mol Pharmacol. Dec. 2010;78(6):1026-35. doi: 10.1124/mol.110.067538. Epub Sep. 9, 2010.

Scanlon et al., Membrane cholesterol modulates serotonin transporter activity. Biochemistry. Sep. 4, 2001;40(35):10507-13.

Schloss et al., Heterogeneity of antidepressant binding sites on the recombinant rat serotonin transporter SERT1. Biochemistry. Oct. 3, 1995;34(39):12590-5.

Serrano-Vega et al., Conformational thermostabilization of the beta(1)-adrenergic receptor in a detergent-resistant form. Proc Natl Acad Sci U S A. Jan. 22, 2008;105(3):877-82. doi: 10.1073/pnas.0711253105. Epub Jan. 11, 2008.

Serrano-Vega et al., Transferability of thermostabilizing mutations between beta-adrenergic receptors. Mol Membr Biol. Dec. 2009;26(8):385-96. doi:10.3109/09687680903208239.

Shibata et al., Thermostabilization of the neurotensin receptor NTS1. J Mol Biol. Jul. 10, 2009;390(2):262-77. doi: 10.1016/j.jmb.2009.04.068. Epub May 5, 2009.

Shimamura et al., Molecular basis of alternating access membrane transport by the sodium-hydantoin transporter Mhp1. Science. Apr. 23, 2010;328(5977):470-3. doi: 10.1126/science.1186303.

Singh et al., Antidepressant binding site in a bacterial homologue of neurotransmitter transporters. Nature. Aug. 23, 2007;448(7156):952-6. Epub Aug. 8, 2007.

Smirnova et al., A mutation in the lactose permease of *Escherichia coli* that decreases conformational flexibility and increases protein stability. Biochemistry. Mar. 18, 2003;42(10):3025-31.

Talvenheimo et al., Solubilization of the platelet plasma membrane serotonin transporter in an active form. J Biol Chem. Sep. 25, 1980;255(18):8606-11.

Tate et al., Comparison of seven different heterologous protein expression systems for the production of the serotonin transporter. Biochim Biophys Acta. Feb. 17, 2003;1610(1):141-53.

Tate et al., Molecular chaperones stimulate the functional expression of the cocaine-sensitive serotonin transporter. J Biol Chem. Jun. 18, 1999;274(25):17551-8.

Tate et al., The effect of N-linked glycosylation on activity of the Na(+)- and Cl(−)-dependent serotonin transporter expressed using recombinant baculovirus in insect cells. J Biol Chem. Oct. 21, 1994;269(42):26303-10.

Tate, A crystal clear solution for determining G-protein-coupled receptor structures. Trends Biochem Sci. Sep. 2012;37(9):343-52. doi:10.1016/j.tibs.2012.06.003. Epub Jul. 10, 2012.

Tate, Baculovirus-mediated expression of neurotransmitter transporters. Methods Enzymol. 1998;296:443-55.

Tate, Overexpression of mammalian integral membrane proteins for structural studies. FEBS Lett. Aug. 31, 2001;504(3):94-8.

Tate, Practical considerations of membrane protein instability during purification and crystallisation. Methods Mol Biol. 2010;601:187-203. doi:10.1007/978-1-60761-344-2_12.

Vinothkumar et al., Structures of membrane proteins. Q Rev Biophys. Feb. 2010;43(1):65-158. doi: 10.1017/S0033583510000041.

Warne et al., The structural basis for agonist and partial agonist action on a β(1)-adrenergic receptor. Nature. Jan. 13, 2011;469(7329):241-4. doi:10.1038/nature09746. Supplementary Information.

White, The progress of membrane protein structure determination. Protein Sci. Jul. 2004:13(7):1948-9.

Yamashita et al., Crystal structure of a bacterial homologue of Na(+)/Cl(−)-dependent neurotransmitter transporters. Nature. Sep. 8, 2005;437(7056):215-23. Epub Jul. 24, 2005.

Zhou et al., Antidepressant specificity of serotonin transporter suggested by three LeuT-SSRI structures. Nat Struct Mol Biol. Jun. 2009;16(6):652-7. doi: 10.1038/nsmb.1602. Epub May 10, 2009.

UniProt Accession No. H2MER2. Mar. 12, 2012. Kasahara et al.

Chen et al., The third transmembrane domain of the serotonin transporter contains residues associated with substrate and cocaine binding. J Biol Chem. Nov. 7, 1997;272(45):28321-7.

Foord et al., International Union of Pharmacology. XLVI. G protein-coupled receptor list. Pharmacol Rev. Jun. 2005;57(2):279-88.

Henry et al., Serotonin and cocaine-sensitive inactivation of human serotonin transporters by methanethiosulfonates targeted to transmembrane domain I. J Biol Chem. Sep. 26, 2003;278(39):37052-63. Epub Jul. 17, 2003.

Henry et al., Tyr-95 and Ile-172 in transmembrane segments 1 and 3 of human serotonin transporters interact to establish high affinity recognition of antidepressants. J Biol Chem. Jan. 27, 2006;281(4):2012-23. Epub Nov. 3, 2005.

Loland et al., Relationship between conformational changes in the dopamine transporter and cocaine-like subjective effects of uptake inhibitors. Mol Pharmacol. Mar. 2008;73(3):813-23. Epub Oct. 31, 2007.

Mao et al., Involvement of serotonin transporter extracellular loop 1 in serotonin binding and transport. Mol Membr Biol. Feb. 2008;25(2):115-27. doi:10.1080/09687680701633257.

| Plasmid DNA (μg per 50,000 cells) | 0.05 | 0.1 | 0.2 | 0.4 | 0.8 |
|---|---|---|---|---|---|
| Plasma membrane expression (%) | 85 | 90 | 70 | 30 | 5 |

FIG. 7A
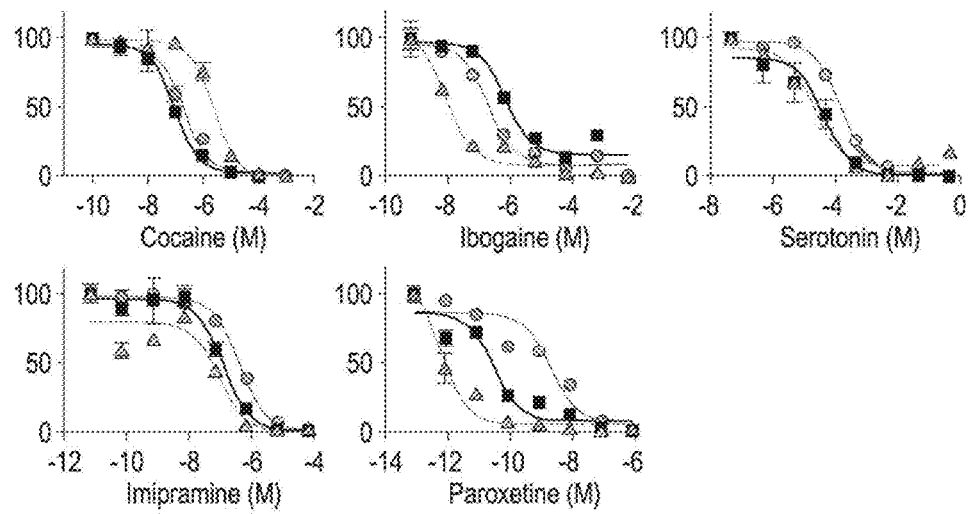
FIG. 7B
| $K_i$ | SAH6 | SAH7 | WT |
|---|---|---|---|
| Cocaine (nM) | 90 ± 17 | 30 ± 21 | 1560 ± 21 |
| Ibogaine (nM) | 90 ± 23 | 330 ± 19 | 20 ± 14 |
| Imipramine (nM) | 0.2 ± 0.24 | 0.06 ± 0.02 | 0.03 ± 0.02 |
| Paroxetine (nM) | 0.9 ± 0.01 | 0.01 ± 0.02 | 0.01 ± 0.02 |
| Serotonin (nM) | 155 ± 37 | 82 ± 30 | 53 ± 22 |
FIG. 7C
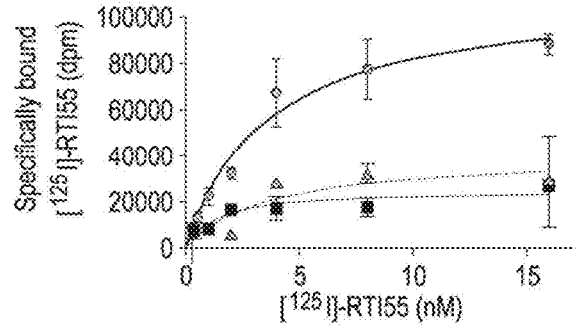

```
SERT    1  METTPLNSQKVLSECKDREDCQENGVLQKGVPTTADRAEPSQISNGYSAVPSTSAGDEAS   60
LeuT    1  ------------------------------------------------------------    0

SERT   61  HSIPAATTTLVAEIRQGERETWGKKMDFLLSVIGYAVDLGNIWRFPYICYQNGGGAFLLP  120
LeuT    1  --------------MEVKREHWATRLGLILAMAGNAVGLGNFLRFPVQAAENGGGAFMIP   46

SERT  121  YTIMAIFGGIPLFYMELALGQYHRNGCISIWRKI------CPIFKGIGYAICIIAFYIAS  174
LeuT   47  YIIAFLLVGIPLMWIEWAMGRYGGAQGHGTTPAIFYLLWRNRFAKILGVFGLWIPLVVAI  106

SERT  175  YYNTIIAWALYYLISSLTDRLPWTSCTNSWNTGNCTNYFAQDNITWTLHSTSPAEEFYLR  234
LeuT  107  YYVYIESWTLGFAIKFLVGLVPEF------------PPNATDPDSILRPFKEFLYS     150

SERT  235  HVLQIHQSKGLQDLGTISWQLTLCIVLIFTVIYFS-IWKGVKTSGKVVWVTATFPYIVLS  293
LeuT  151  YIGVFKGDEPILKPSLFAYIVFLITMFINVSILIRGISKGIERFAKIAMPTLFILAVFLV  210

SERT  294  VLLVRGATLPG-AWRGVVFYLKPNWQKLLETGVWVDAAAQIFFSLGPGFGVLLAFASYNK  352
LeuT  211  IRVFLLETPNGTAADGLNFLWTPDFEKLKDPGVWIAAVGQIFFTLSLGFGAIITYASYVR  270

SERT  353  FNNNCYQDALVTSVVNCMTSFVSGFVIFTVLGYMAEMRNEDVSEVAKDAGPSLLFITYAE  412
LeuT  271  KDQDIVLSGLTAATLNEKAEVILGGSISIPAAVAFFG-VANAVAIAKAGAFNLGFITLPA  329

SERT  413  AIANMPASTFFAIIFFLMLITLGLDSTFAGLEGVITAVLDEFPHIWAKRREWFVLIVVIT  472
LeuT  330  IFSQTAGGTFLGFLWFFLLFFAGLTSSIAIKQPMIAFLEDELKLSRKHAVLWTAAIVFFS  389

SERT  473  CVLGSLLTLTSGGAYVVTLLEEYATGPAVLTVALIEAVAVSWFYGITQFCSDVKEMLGFS  532
LeuT  390  AHLVMFLN------KSLDEMDFWAGTIGVVFFGLTELIIFFWIFGADKAWEEINRGGIIK  443

SERT  533  PGWFWRICWVAISPLFLLFIICSFLMSPPQLRLFQYNYPHWSIVLGYCIGMSSVICIPTY  592
LeuT  444  VPRIYYYVMRYITPAFLAVLLVWAREYIPKIMEETHWTWITRF-YIIGLFLFLTFLVP   502

SERT  593  IIYR--LISTPGTLKERIIKSITPETPTEIPCGDIRMNAV                    630
LeuT  503  LAERRRNHESAGTLVPR------------------------                   519
```

FIG. 9

FIG. 10A
FIG. 10B
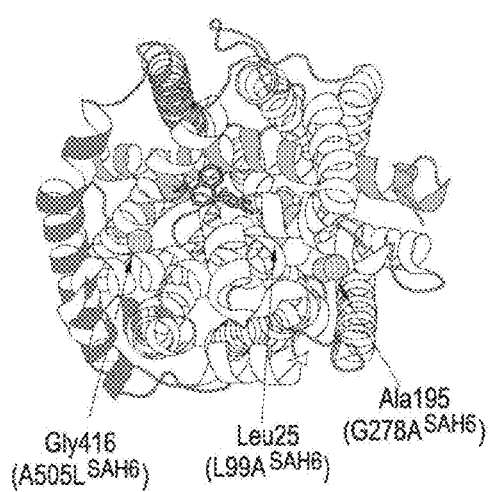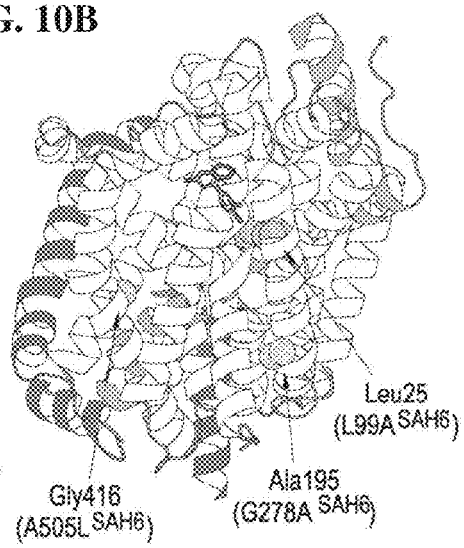
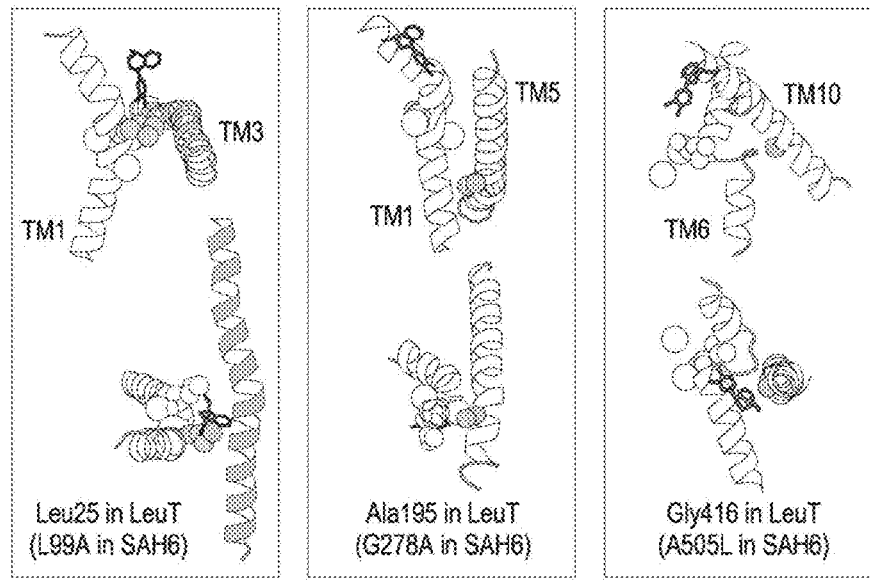
FIG. 10C

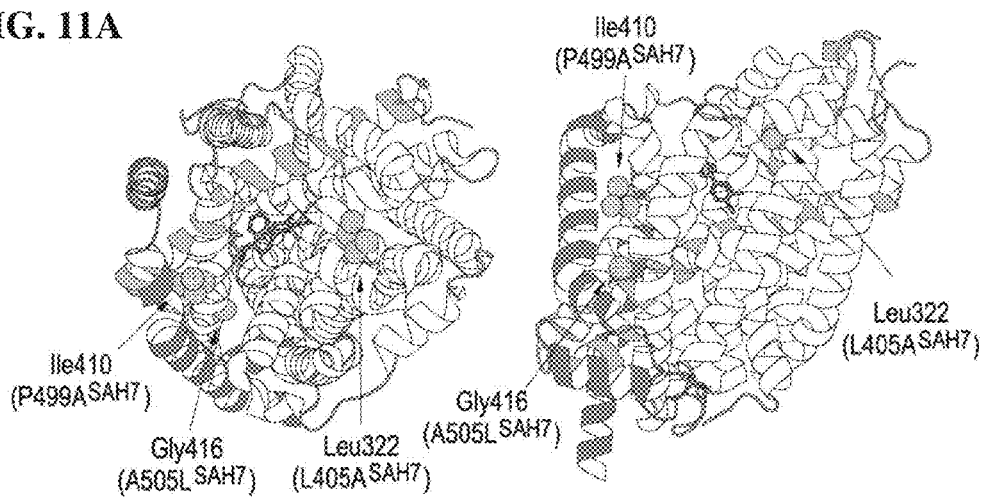
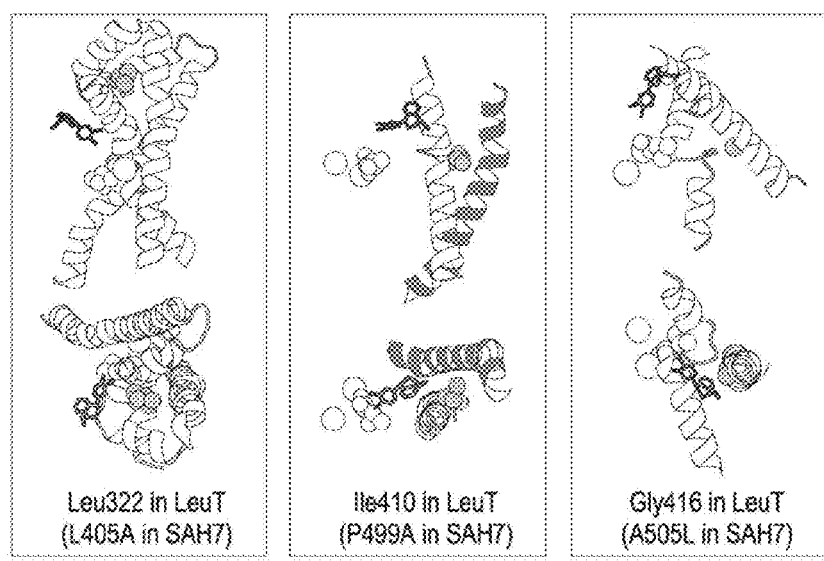
FIG. 11A
FIG. 11B
FIG. 11C

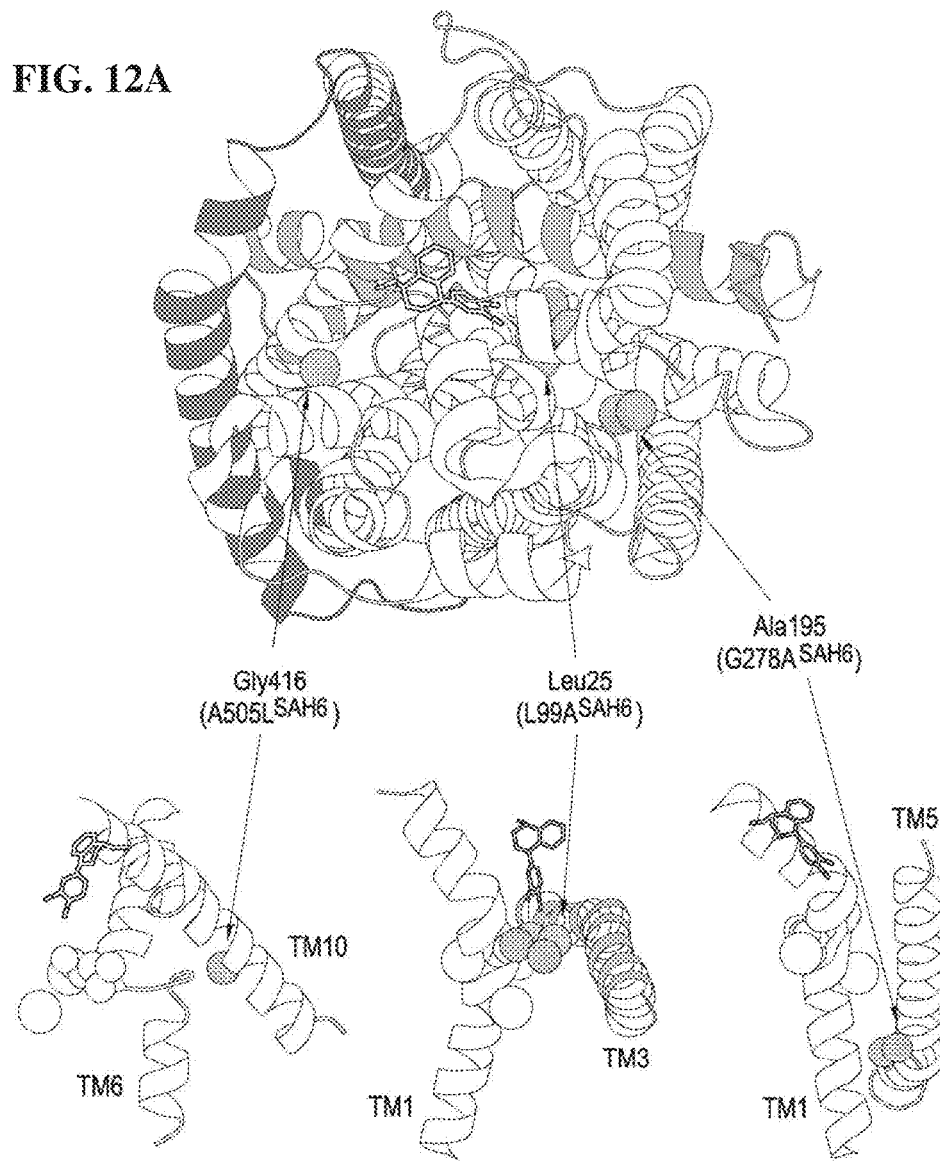
FIG. 12A
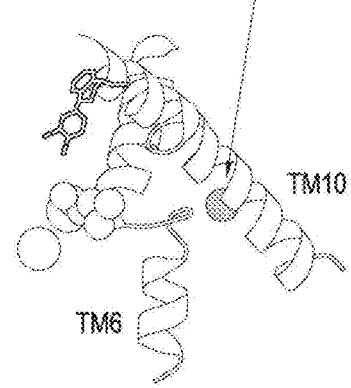
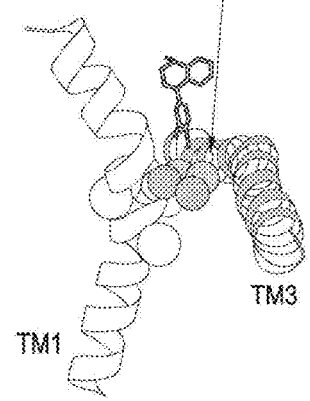
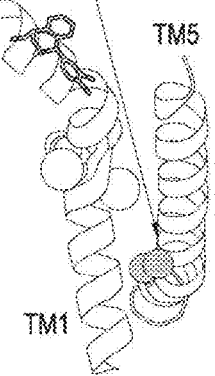
FIG. 12B  FIG. 12C  FIG. 12D

MUTANT PROTEINS AND METHODS FOR THEIR PRODUCTION

The present invention relates to mutant transmembrane proteins which have increased conformational stability when compared to their parent protein, methods of selection and production. In particular the invention relates to mutant transmembrane proteins which are mutated in or in the proximity of the transmembrane alpha helices or in a kinked region or in an alpha-helix adjacent to a kink. The mutant transmembrane proteins have use in crystallisation studies and also in screening to identify compounds for use in drug discovery and therapy.

BACKGROUND TO THE INVENTION

Structure determination of eukaryotic integral membrane proteins is challenging and techniques and strategies developed recently has underpinned GPCR crystallization, including the development of receptor-T4 lysozyme (T4L) fusions (1,2), conformational thermostabilisation of GPCRs (3-7), and the use of antibody fragments (8-10).

However, the key component for successful crystallization is the stability of the GPCR during purification and crystallization (11). Techniques such as the addition of high affinity ligands to receptor-T4L fusions, and systemic mutagenesis coupled to a thermostability assay (3, 4, 6, 7) have improved the stability of GPCRs in detergent solution, detergent-stability being an essential prerequisite to purification and crystallisation. The latter approach locks the receptor in a particular conformation which allows successful crystallization as described in WO2008/114020 and WO2009/071914, and also has the advantage that the crystal structure of the GPCR bound to ligands that bind only very weakly can be determined (12,13). As described in WO2009/071914 it was found that stabilising mutations identified in one GPCR could be transferred to another GPCR by aligning the amino acid sequence thus generating a second GPCR with increased stability. However the positions of the stabilising mutations were not located in a common motif or region but instead scattered throughout the GPCR (the turkey β1-adrenergic receptor, human adenosine receptor, rat neurotensin receptor and human muscarinic receptor).

In recent years most success in obtaining crystal structures of membrane proteins has been for bacterial proteins (14) since these are easier to overexpress using known techniques in *Escherichia coli* than eukaryotic membrane proteins (15, 16) and are more likely to exhibit stability in detergent solution. In contrast eukaryotic membrane proteins often have poor stability in detergent solutions which severely restricts the range of crystallisation conditions that can be explored. Although the structures of over 300 unique polytopic integral membrane proteins have been determined (blanco.biomol.uci.edu/), less than 10% are eukaryotic and approximately half were purified from natural sources and are stable in detergent solutions.

Transmembrane transporters are similar to GPCRs because they exist in at least two distinct conformations, with the substrate binding site accessible to either the extracellular environment (outward-open) or to the cytoplasm (inward-open), with a number of potential intermediate occluded states where the substrate cannot dissociate to either side of the membrane (40). Indeed, the structures of many bacterial transporters have been determined that fit into the above scheme and, at least in the case of Mhp1 (41) and LeuT (26) different conformations of the same transporter have also been described. Transmembrane transporters have been less widely studied than GPCRs but nevertheless are highly relevant in human physiology and disease. They represent valuable targets in drug discovery and development of therapeutics, for example the monoamine transporters are key targets for therapeutic intervention in a wide range of CNS disorders and as primary targets for drugs of abuse such as cocaine and amphetamines (17, 18). Two of the most widely prescribed drugs fluoxetine (Prozac) and omeprazole (Prilosec) target membrane transporters, and there is a need in the art to understand further the structure and function of transmembrane transporters and their role in disease to meet the demand for new therapies targeting CNS disorders.

Current methodologies for the crystallisation of transporters have relied on the identification of those transporters that are sufficiently stable for purification and crystallisation (19) which has allowed the structure determination of many transporters from different families, but the majority of the structures are of bacterial proteins (20). To fully understand inhibitor binding and the mechanism of transport of the mammalian transporters it is essential to determine their structures. However the mammalian transporters are difficult targets for structural studies due to low levels of functional expression and only a proportion of the expressed protein is correctly folded (21, 22). Heterologous expression of the cocaine-sensitive rat serotonin transporter (SERT), GABA (GAT) and norepinephrine (NET) is possible in baculovirus systems however functional expression levels are low and only a proportion of the expressed protein is correctly folded according to the binding of radiolabelled inhibitors (23, 24).

The SLC6 transporter is a sub-class of the neurotransmitter sodium symporter family (NSS) (25) and plays an important role in regulating neurotransmitter concentrations in the peripheral and central nervous system by re-uptake into the presynaptic nerve termini. Mammalian SLC6 is characterised by 12 transmembrane helices with a large extracellular loop between transmembrane helices 3 and 4 (TM3 and TM4) that is invariably N-glycosylated. Structural studies on this family of transporters has focused on bacterial homologues that are extremely stable, such as LeuT (26).

Lactose permease of *E. coli* (LacY) has been the focus of a number of studies relating to structure and functionality and the crystal structure has been solved using a mutant (C154G) which renders the protein unable to undergo the structural changes required for transport of sugar across the membrane. The mutation (Cys154 to Gly) causes a more compact structure and decreased conformational flexibility with improved thermostability and little tendency to aggregate. It was also observed that the conformational change caused little or no effect on ligand binding (38). These studies demonstrate that it is possible to obtain a conformationally thermostabilised transporter membrane protein by way of mutation which is suitable for crystallisation. (39). Although these studies are of importance for Lactose Permease they do not comment on the wider problem of how to reliably and efficiently solve the crystal structures of other transporter proteins and GPCRs. Therefore there is a need for a common strategy to produce conformationally stable proteins that have use in crystallisation studies and structure determination. Since the provision of conformationally stable mutants of transporters and/or GPCRs and subsequent screening is time consuming, there is a need for methods that are more efficient and reduce the time taken to produce a conformationally stable mutant.

In view of the difficulty in obtaining high quality crystal structures of mammalian proteins due to poor stability and expression and the low numbers of solved crystal structures, there is a need to produce new methods and techniques that overcome the above-mentioned problems, particularly for membrane transporters which as yet have not benefited from the intensity of research seen for GPCRs.

The cocaine-sensitive rat serotonin transporter (SERT) is a member of the SLC6 sub-class of the neurotransmitter sodium symporter family (NSS) and transports the neurotransmitter serotonin from synaptic spaces into presynaptic neurons thereby terminating the action of serotonin. SERT has been well characterised in terms of physiological function and is the target of many antidepressant medications, however its crystal structure remains to be determined. SERT is known to be unstable in detergent solution (27) making it a challenging target for thermostabilisation studies, however the availability of a high affinity radiolabelled ligand [$^{125}$I] RTI55 (β-CIT) allows dicrimination between functional and misfolded protein making the protein a suitable candidate for thermostabilisation studies.

The inventors have applied the conformational thermostabilisation approach recently used for GPCRs to the cocaine-sensitive rat serotonin transporter (SERT) to improve conformational stability and tolerance in detergent. They found that when particular regions in or nearby the alpha helices of the transmembrane regions of integral membrane proteins are mutated, this results in a higher proportion of conformationally stable mutants. This discovery has significance for structure determination of other related membrane proteins since it is possible that mutations in specific regions of a membrane protein can be applied across a range of membrane proteins having similar three-dimensional structures, thereby improving the probability of obtaining conformationally stable mutants for use in crystallisation.

SUMMARY OF THE INVENTION

According to a first aspect of the invention there is provided a mutant transmembrane protein which has increased conformational stability compared to its parent transmembrane protein, wherein the one or more mutations are located at the interfaces between transmembrane alpha-helices, or in a kinked region or in an alpha-helix adjacent to a kink.

According to a further aspect of the invention there is provided a method of selecting a mutated transmembrane protein comprising the steps of;
a) Providing one or more mutants of a parent transmembrane protein wherein the mutations are at the interfaces between transmembrane alpha-helices, or in a kinked region or in an alpha-helix adjacent to a kink.
b) Contacting the mutated transmembrane protein with a ligand
c) Determining the thermostability of the mutated transmembrane protein
d) Identifying those mutants that exhibit increased conformational thermostability compared to the parent transmembrane protein According to a further aspect of the invention there is provided a method of producing a mutated transmembrane protein comprising carrying out the steps a) to d) and,
e) Identifying the position of one or more of the mutated amino acid residues in those mutants that exhibit increased conformational stability, and f) Synthesising a mutant transmembrane protein which comprises the mutated residues identified in step e).

According to a further aspect of the invention there is provided a method of selecting a binding partner of a mutated transmembrane protein, the method comprising the steps of
a) providing a mutant transmembrane protein which has increased conformational stability and/or is functionally inactive compared to its parent transmembrane protein, wherein the one or more mutations are located at the interfaces between transmembrane alpha-helices, or in a kinked region or in an alpha-helix adjacent to a kink.
b) contacting the mutant transmembrane protein with one or more compounds
c) determining whether the one or more compounds bind to the mutant transmembrane protein
d) isolating one or more compounds.

According to a further aspect of the invention there is provided a mutant transmembrane protein obtained by the methods of the previous aspects.

BRIEF DESCRIPTION OF THE FIGURES

(FIG. 1A) The amount of tetracycline used to induce cells transiently transfected with SERT-mCherry was tested to give good cell surface expression with minimal intracellular expression, as defined by confocal microscopy. Examples of cells depicted were either induced with 1.2 µg/ml tetracycline (left hand panel) or 0.8 µg/ml tetracycline (right-hand panel). Cells were transfected with 0.1 mg of plasmid DNA per 50,000 cells and were induced for 48 hours. (FIG. 1B) The DNA:transfection reagent ratio for maximal correctly localised expression of SERT. 50,000 cells were transfected with a range of DNA concentrations. Cells were induced with 0.8 µg/ml tetracycline for 48 hours, examined using a confocal microscope and the percentage of plasma membrane expression of SERT was estimated by eye.

(FIG. 2A) The thermostability of [$^{125}$I]-RTI55-bound SERT was determined after solubilisation in three different concentrations of DDM (final concentrations in %): squares, 0.01%; triangles, 0.1%; circles, 1%. The difference in thermostability is likely a consequence of the degree of delipidation of the transporter that increases as the amount of detergent increases. Each data point (±SEM) was obtained in duplicate from an equivalent of 50,000 cells from a tetracycline-induced stable cell line T-Rex-SERT. (FIG. 2B) Thermostability assays of SERT-His10 expressed in the stable cell line T-Rex-SERT (circles) and SERT-mCherry transiently transfected into T-Rex-HEK293 cells (squares). Cells were solubilised with 0.1% DDM after the addition of 1 nM [$^{125}$I]-RTI55; the apparent Tm of both samples of SERT was 28° C. All the reactions contained the equivalent of 50,000 cells per data point. The results are from a single experiment performed in duplicate (±SEM).

(FIG. 3B) The optimally thermostabilised SAH mutants were engineered by combining the best thermostabilising mutations (as indicated) which resulted in an increased apparent $T_m$ after solubilisation in 0.1% DDM. (FIG. 3C) Amino acid sequence of SERT (SEQ ID NO: 1) showing the positions of the thermostabilising mutations (hatched) that consistently gave >1° C. increase in $T_m$ compared to wild-type SERT; residues in bold and hatched were used to stabilize either SAH6 and/or SAH7. N-linked glycosylation sites are indicated by the hexagons, a putative disulphide bond is shown as a grey line and the N-terminal and C-terminal fusion partners are shown (c-Myc tag and the fluorescent reporter protein mCherry) are indicated.

Amino acid residues already identified as being thermostabilising in the preliminary Ala/Leu scan were changed either to Ala, Gly, Val Leu or Ile (hatched). Where no functional SERT was detected, the amino acid to which the residue was mutated is given in the single letter code. Bars marked with an asterisk showed improved thermostability over the original mutation, but expression levels were less than 10% of the wild type SERT and therefore these mutations were not used further.

Figure 5A:
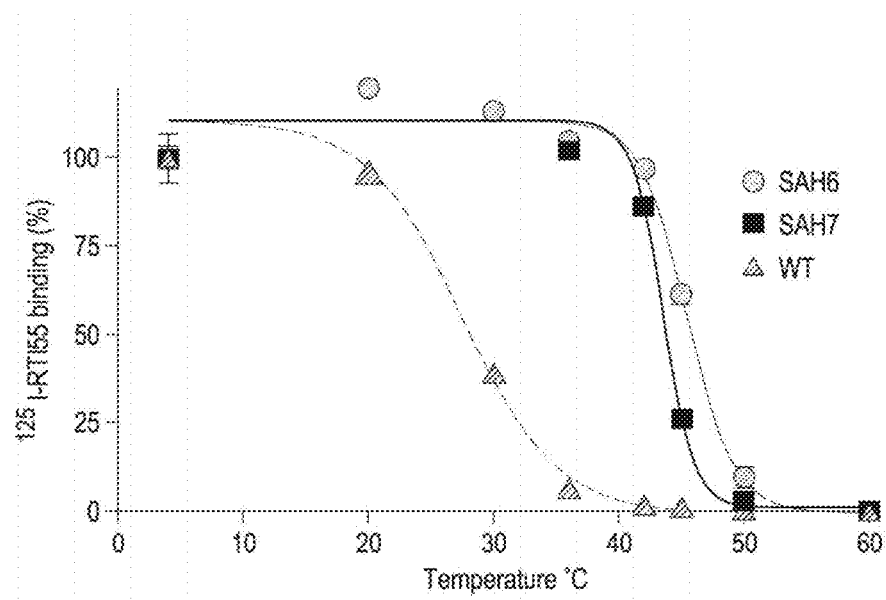
Figure 5B:
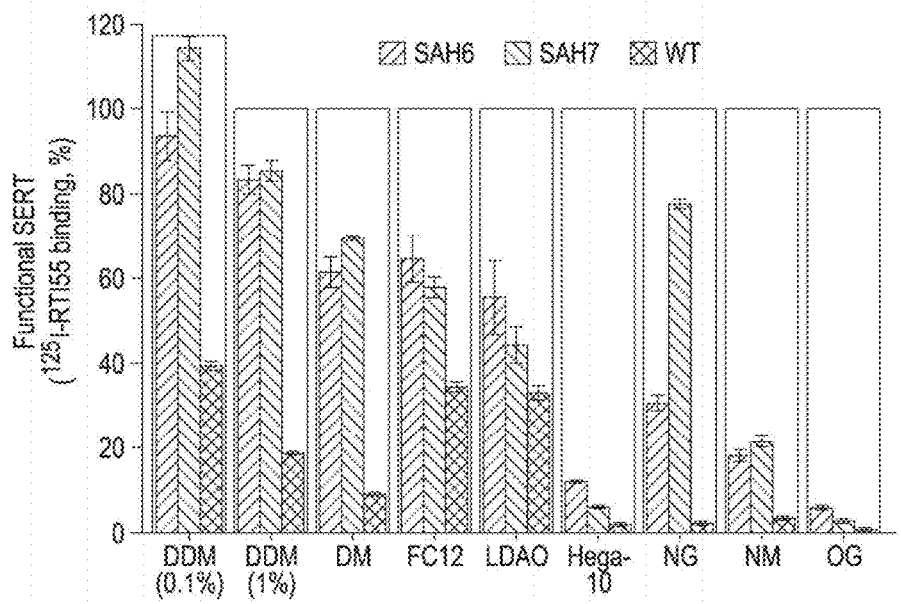

FIGS. 5A-5B Detergent stability of the thermostabilised mutants SAH6 and SAH7.

(FIG. 5A) Thermostability curves for [$^{125}$I]-RTI55-bound DDM-solubilised SAH6 (circles) and SAH7 (squares) compared to wild-type SERT (triangles). The apparent $T_m$s determined from the curves are: SAH6, 46° C.; SAH7, 44° C.; wild-type SERT, 28° C. All the data were collected in a single experiment with measurements performed in duplicate. (FIG. 5B) The stability of [$^{125}$I]-RTI55-bound SAH6, SAH7 and wild-type SERT was compared in 8 different detergents [$^{125}$I]-RTI55 was added to membranes (final concentration 1 nM) which were then solubilised for 30 min on ice in the following detergents (aliphatic chain length in parentheses, final detergent concentration in %): 0.1% DDM (C12), 1% DDM (C12), 0.4% DM (C10), 0.35% FC12 (C12), 0.3% LDAO (C12), 0.6% Hega-10 (C10), 0.5% NG (C9), 0.6% NM (C9), 0.83% OG (C8). The detergent-solubilised samples where then heated at 30° C. for 30 min before determining the amount of SERT remaining in relation to control (incubated on ice). Results are from a single experiment performed in duplicate (±SEM) with the equivalent of 50,000 cells per data point.

Figure 6:
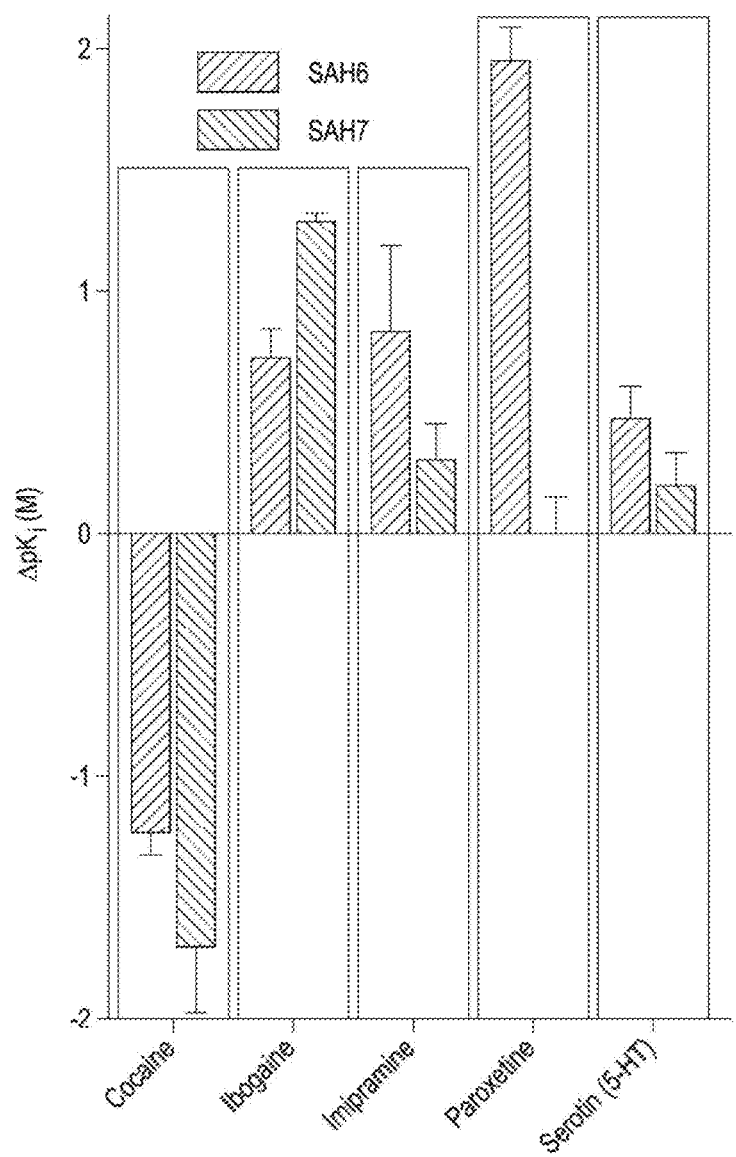

FIG. 6 Inhibitor and substrate affinities for SAH6 and SAH7 mutants compared with wild-type SERT.

Apparent $K_i$ values were determined from competition binding curves (FIGS. 7A-7C) and are plotted as the change in affinities with respect to wild-type SERT ($\Delta pK_i$). Competition assays were performed on membranes using a final concentration of 0.2 nM [$^{125}$I]-RTI55 and apparent $K_i$ values determined using the following apparent $K_D$ values for [$^{125}$I]-RTI55 binding (FIGS. 7A-7C): SAH6, 3.7±0.7 nM; SAH7, 1.2±0.5 nM; wild-type SERT, 3.7±2.2 nM. Error bars are proportional to the SEM from the original measurements.

FIGS. 7A-7C Competition curves for SAH6 and SAH7.

(FIG. 7A) Competition assays were performed on membranes using a final concentration of 0.2 nM [$^{125}$I]-RTI55 and apparent $K_i$ values (FIG. 7B) were determined using the following apparent $K_D$ values for [$^{125}$I]-RTI55 binding (FIG. 7C): SAH6, 3.7±0.7 nM; SAH7, 1.5±0.6 nM; wild-type SERT, 3.7±2.2 nM. All results were obtained from two independent experiments performed in duplicate (±SEM). For all graphs: wild type SERT, triangles; SAH6, circles; SAH7, squares.

Figure 8A:
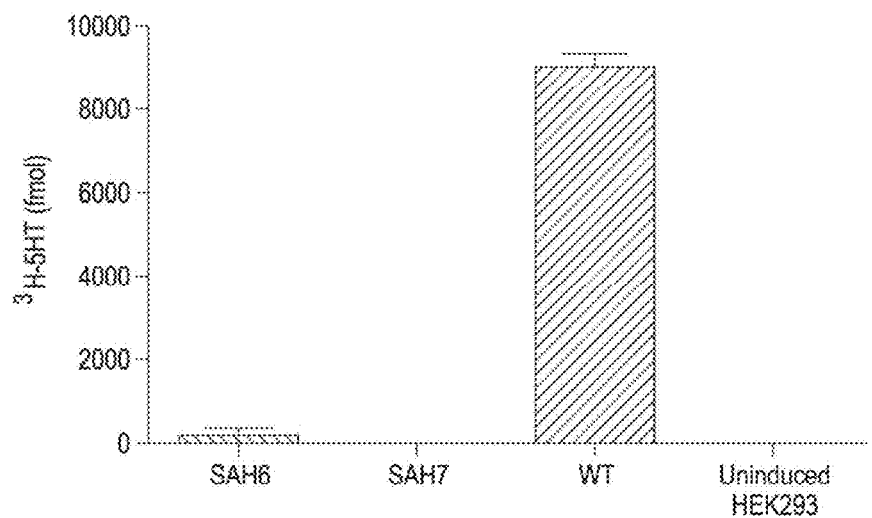
Figure 8B:
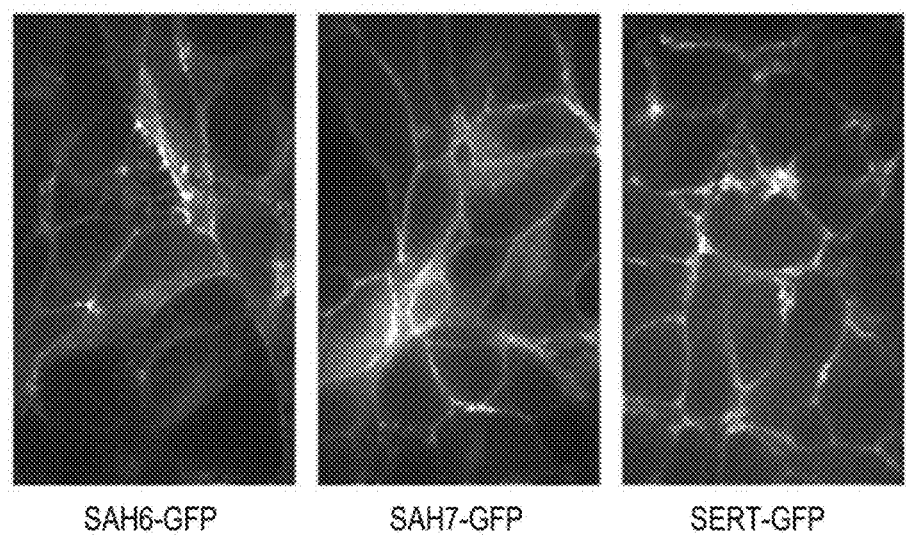
Figure 13A:
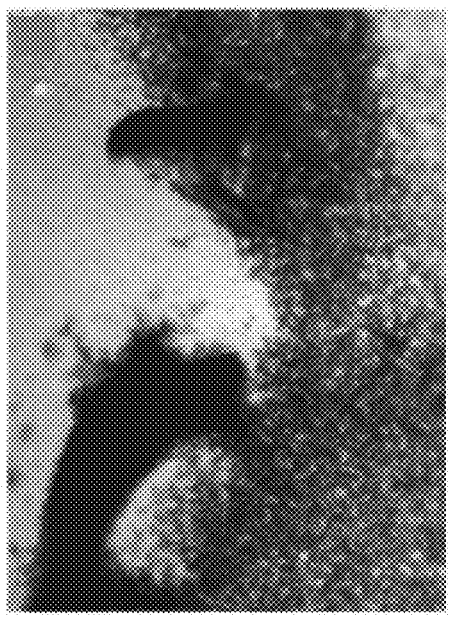
Figure 13B:
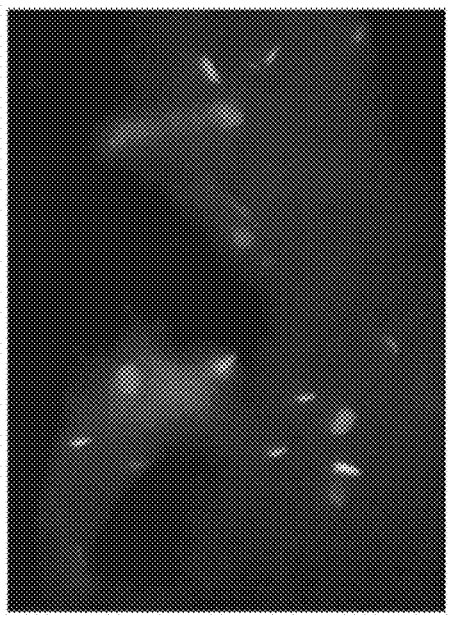
Figure 13C:
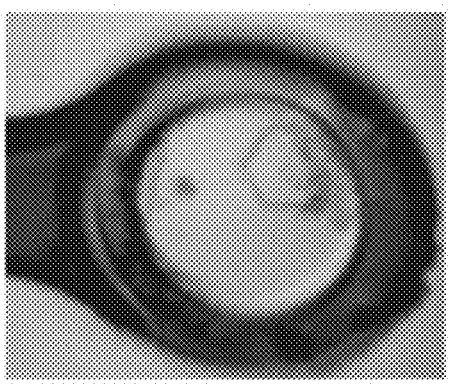
Figure 13D:
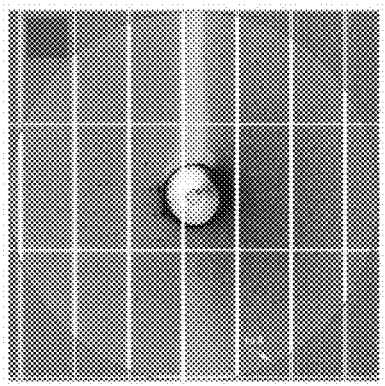

FIGS. 8A-8B Thermostabilised mutants do not transport 5HT.

(FIG. 8A) [$^3$H]5HT uptake assays were performed on tetracycline-induced stable T-REx cell lines expressing SAH6-GFP, SAH7-GFP, and SERT-GFP, with non-specific uptake determined upon addition of 10 mM cocaine and the results baseline corrected. The results are from a single experiment performed in triplicate (±SEM) with approximately 100,000 cells per data point. (FIG. 8B) Confocal microscope images of cells expressing transporter-GFP fusions used in the uptake assays in (FIG. 8A). No fluorescence was detected in parental T-REx-HEK293 cells. SAH6-GFP, SAH7-GFP and SERT-GFP were all capable of binding [$^{125}$I]-RTI55-binding with high affinity (FIGS. 7A-7C).

FIG. 9 Amino acid sequence alignment between *Rattus norvegicus* SERT and *Aquifex aeolicus* LeuT (19% identity).

Identical residues (*) and similar residues (.) are indicated below the aligned amino acid sequences (SERT, SEQ ID NO: 1; LeuT, SEQ ID NO: 2). The transmembrane alpha-helices in LeuT (as defined by the structure) are shown as grey shading, with unwound regions as a grey line, and other alpha-helices are shown as hatched bars. The positions of the 11 thermostable mutations are shown either as hatched (present in SAH6 and/or SAH7) or hatched and shaded (other thermostabilising mutations).

FIGS. 10A-10C Equivalent positions in LeuT of the thermostabilising mutations in SAH6.

A cartoon of LeuT (PDB code 3GWU) is shown in black and white (N terminus light shade, C-terminus dark shade) with bound leucine (hatched spheres), Na+ ions (spheres) and sertraline (sticks). Shaded spheres indicate amino acid side chains in LeuT that are equivalent to the thermostabilising mutations found in SAH6 (in parentheses): Leu25 (L99A); Ala195 (G278A); Gly416 (A505L). LeuT is shown either viewed from the extracellular surface of the membrane (FIG. 10A) or parallel to the membrane plane (FIG. 10B). Portions of the structures have been highlighted (boxes, FIG. 10C) to depict the position of the residues in relation to helix-helix interfaces.

FIGS. 11A-11C Equivalent positions in LeuT of the thermostabilising mutations in SAH7.

A cartoon of LeuT (PDB code 3GWU) is shown in black and white (N terminus light shade, C-terminus dark shade) with bound leucine (hatched spheres), Na+ ions (spheres) and sertraline (sticks). Shaded spheres indicate amino acid side chains in LeuT that are equivalent to the thermostabilising mutations found in SAH7 (in parentheses): Leu322 (L405A); Ile410 (P499A); Gly416 (A505L). LeuT is shown either viewed from the extracellular surface of the membrane (FIG. 11A) or parallel to the membrane plane (FIG. 11B). Portions of the structures have been highlighted (boxes, FIG. 11C) to depict the position of the residues in relation to helix-helix interfaces.

FIGS. 12A-12D Amino acid residues in LeuT equivalent to the thermostabilising mutations in SAH6. (FIG. 12A) The structure of LeuT (PDB code 3GWU) is depicted in black and white (N terminus, light shade; C-terminus, dark shade) with the side chains in equivalent positions to the thermostabilisation mutations in SAH6 shown as shaded spheres. The view is from the extracellular surface perpendicular to the membrane plane. (FIGS. 12B-12D) The mutations are found at helix-helix interfaces and often at the sites of kinks or unwound regions; (FIG. 12B) Gly416$^{LueT}$ (A505L$^{SAH6}$); (FIG. 12C) Leu25$^{LeuT}$ (L99A$^{SAH6}$); (FIG. 12D) Ala195$^{LeuT}$ (G278A$^{SAH6}$). Additional views of the mutations are in FIGS. 10A-10C and for details of SAH7 mutations, see FIGS. 11A-11C.

FIGS. 13A-13D Crystallisation of thermostabilised SERT (FIG. 13A) Crystallisation drop viewed under white light. (FIG. 13B) The same area of the crystallisation drop viewed under UV light where protein crystals appear white on a dark background. (FIG. 13C) One crystal mounted on a loop for collection of X-ray diffraction patterns. (FIG. 13D) One X-ray diffraction pattern showing diffraction spots to 8 Å resolution (the ring shows the 7.5 Å diffraction limit).

DETAILED DESCRIPTION OF THE INVENTION

According to a first aspect of the invention there is provided a mutant membrane protein which has increased conformational stability compared to its parent membrane protein, wherein the one or more mutations are located at the interfaces between transmembrane alpha-helices, or in a kinked region or in an alpha-helix adjacent to a kink.

References herein to "membrane protein" refer to a protein that is attached to or associated with a membrane of a cell or organelle. Examples of membrane proteins include GPCRs, T-cell receptors, growth factor receptors, transmembrane ion channels, transmembrane transporters, a ligand-gated transmembrane ion channel, a voltage-gated transmembrane ion channel, an enzyme, a carrier protein or an ion pump. Membrane proteins may comprise more than one polypeptide chain.

For example the membrane protein may be an integral membrane protein that is permanently integrated into the membrane and can only be removed by using detergents, non-polar solvents or denaturing agents that physically disrupt the lipid bilayer.

References to "transmembrane protein" herein refer to an integral membrane protein which extends from one side of the membrane through to the other side of the membrane, thus spanning the entire membrane.

References to "transmembrane transporters" herein refer to transmembrane proteins which are responsible for the transport of ions, small molecules or macromolecules across a membrane. Suitable transmembrane transporters include monamine transporters, for example the cocaine-sensitive rat serotonin transporter (SERT), the dopamine transporter (DAT) and the norepinephrine transporter (NET).

In one embodiment the membrane protein is an integral membrane protein or a transmembrane protein.

In another embodiment the membrane protein is a transmembrane transporter or a GPCR.

In another embodiment the transmembrane transporter is a monamine transporter.

In a further embodiment the transmembrane transporter is a member of the SLC6 sub-class of the neurotransmitter sodium symporter family (NSS).

In a further embodiment the transmembrane transporter is the cocaine-sensitive rat serotonin transporter (SERT).

The membrane protein may be derived from any source, for example a eukaryotic source, a prokaryotic source, or from cell-free systems.

In one embodiment the membrane protein is mammalian and derived from rat, mouse, rabbit, dog, or non-human primate, man, chicken or turkey.

Suitable GPCRs are well known in the art and include those listed in Foord et al (2005) *Pharmacol Rev.* 57, 279-288, incorporated herein by reference, (which is periodically updated at iuphar-db.org/DATABASE/ReceptorFamiliesForward?type=GPCR).

Reference to "mutant membrane protein" herein refers to a membrane protein with a different genotype to the wild type (or parent) membrane protein. Such a mutant may also result in a different phenotypic difference.

Reference to "Parent membrane protein" herein refers to a protein which retains a functional activity of the naturally occurring protein. Functional activity may be for example, ligand binding and/or the transport of ions, small molecules or macromolecules across the membrane. The parent membrane protein may be more or less conformationally stable than the mutant membrane protein.

Mutants of the membrane protein may be produced by any suitable method where each amino acid of the parent membrane protein is independently changed to a different amino acid residue. Molecular biological techniques for cloning and engineering genes and cDNAs, for mutating DNA, and for expressing polypeptides from polynucleotides in host cells are well known in the art as exemplified "Molecular cloning, a laboratory manual", third edition, Sambrook, J. & Russell, D. W. (eds), Cold Spring Harbor Laboratory press, Cold Spring Harbor, N.Y., incorporated herein by reference.

Mutations may be made in any part of the membrane protein, for example in the part which spans the membrane.

In one embodiment the mutant membrane protein is produced by alanine scanning mutagenesis, a technique well known in the art. Here each selected amino acid is replaced in turn with alanine to produce a series of mutants suitable for screening. If the selected amino acid is Ala it is replaced with Leu or Gly. Selected regions of the membrane protein may be chosen for alanine mutagenesis, for example amino acid residues 49 to 603 inclusive for SERT.

In another embodiment the mutant membrane protein is produced by random mutagenesis, which may be in the whole of the protein or in a selection part. Such techniques are well known in the art (Asubel et al, *Current Protocols in Molecular Biology*, John Wiley & Sons, New York 2000).

In one embodiment the mutant membrane protein comprises one or more mutations located at the interfaces between transmembrane alpha-helices, or in a kinked region or in an alpha-helix adjacent to a kink. The mutant membrane protein may also comprise one or mutations which are at the sites of unwound regions of the alpha-helix.

References to "transmembrane alpha-helices" herein refer to the helical three-dimensional amino acid structure found within the transmembrane spanning domains of a membrane protein. Transmembrane alpha-helices may be in the form of a single alpha-helix spanning the membrane, a pair of helices or any number of helices passing through the membrane typically ranging from one to twenty-four with common arrangements typified by seven helices passing through the membrane, as in GPCRs, or twelve helices passing through the membrane as in many transporters.

Reference to "interfaces" between transmembrane alpha-helices refers to the regions which are between the strands of the alpha-helix as arranged in the membrane, also known as helix-helix interfaces. Specifically interfaces are defined as regions were the atoms of amino acids residues in two or more separate helices are within van der Waals radii of each other.

Reference to "kinked region" herein refers to the regions which represent a turn of the alpha-helix as arranged in the membrane such that as a result of the kink the helix no longer has a linear conformation but instead comprises a bend or curve.

In one embodiment the mutant membrane protein comprises one or more replaced amino acids compared to the parent membrane protein. In another embodiment the mutant membrane protein comprises two, three, four, five, six or seven replaced amino acids compared to the parent membrane protein. In a further embodiment the mutant membrane protein comprises between two and four replaced amino acids compared to the parent membrane protein. In a further embodiment the mutant membrane protein comprises three or four replaced amino acids compared to the parent membrane protein.

In another embodiment the mutant membrane protein is the cocaine-sensitive rat serotonin transporter (SERT) and comprises at least one of the mutations selected from P499A, A505L, G113A, L99A, G278A, A169L, F311A, G115A, L405A and L406A.

In another embodiment the mutant cocaine-sensitive rat serotonin transporter (SERT) and comprises two, three or four of the mutations selected from P499A, A505L, G113A, L99A, G278A, A169L, F311A, G115A, L405A and L406A.

In another embodiment the mutant membrane protein is the cocaine-sensitive rat serotonin transporter (SERT) and comprises at least one of the mutations selected from G278A, A505L, L99A and P499A.

In a further embodiment the mutant membrane protein is the cocaine-sensitive rat serotonin transporter (SERT) and comprises the mutations L99A, G278A and A505L.

In a further embodiment the mutant membrane protein is the cocaine-sensitive rat serotonin transporter (SERT) and comprises the mutations L405A, P499A and A50L.

In another embodiment the mutant membrane protein comprises at least one or more mutations which are at the corresponding amino acid positions of P499A, A505L, G113A, L99A, G278A, A169L, F311A, G115A, L405A and L406A as defined in the amino acid sequence of SERT shown in FIG. 9.

By "corresponding amino acid position or positions" we mean the position in the amino acid sequence of SERT which aligns to the position in the amino acid sequence of the membrane protein when the sequence of SERT and a membrane protein are compared by alignment using, for example, MacVector and the Clustal W program. Such alignment techniques are known in the art and appreciated by the skilled person.

In a further embodiment the mutant membrane protein comprises at least one or more mutations which are within a window of amino acids either side of the of the position which corresponds to the amino acid positions of one or more of P499A, A505L, G113A, L99A, G278A, A169L, F311A, G115A, L405A and L406A.

A "window of amino acids" refers to a window of i plus or minus four amino acid residues where i is defined as the stabilising mutation.

The stability of the mutant membrane protein is compared to the parent or wild type membrane protein to establish if the presence of the one or more mutations results in an increase in conformational stability.

Reference to "conformational stability" herein refers to the conformation adopted by a membrane protein that results in an improved stability with respect to any one of biological activity of the membrane protein such as binding activity, a signalling pathway modulation activity, a transmembrane transporting activity or an enzyme activity.

Increased conformational stability may be observed when the mutant membrane protein is bound to a ligand. A ligand may function as an inhibitor, an agonist or an antagonist. Ligand binding may cause the mutant membrane protein to reside in a particular conformation, for example with respect to GPCRs, an agonist or antagonist conformation depending on whether the ligand functions as an agonist or antagonist. Thus the presence of the ligand may be considered to encourage the GPCR to adopt a particular conformation. As a function of the ability of membrane transporters to facilitate the vectorial movement of substrates across biological membranes, they can exist in two different conformations known as the outward-open conformation and the inward-open conformation. Ligand binding may influence which conformation the membrane transporter resides in. In this respect, ligand binding that blocks or prevents transport of substances across the membrane functions as an inhibitor. Antibodies, including fragments and derivatives thereof, may function as ligands and induce conformational change in GPCRs and membrane transporters. Antibodies may be specific for a particular conformation of a GPCR or membrane transporter.

In one embodiment the mutant membrane protein is a membrane transporter and is conformationally stabilised in a single conformation such as the outward-open conformation or the inward-open conformation when bound to a ligand.

In another embodiment the mutant membrane transporter is SERT and is conformationally stabilised in the outward-open conformation when bound to a ligand, for example RTI55 (β-CIT).

The ligand may be detectably labelled in accordance with techniques known in the art. For example the ligand is radiolabelled or conjugated to a fluorescent label.

The mutant membrane protein may have an increased stability to any one or more of heat, a detergent, a chaotropic agent and extreme of pH.

Increased stability to heat (i.e. thermostability) can be readily determined by measuring ligand binding or by using spectroscopic techniques such as fluorescence, CD or light scattering at a particular temperature. In one embodiment the thermostability of a mutant membrane protein is determined by measuring the $T_m$ (the temperature at which 50% of the mutant membrane protein is inactivated under certain conditions for a given period of time (e.g. 30 minutes). Mutant membrane proteins having a higher thermostability have higher $T_m$ values when compared to the parent membrane protein.

To determine increased stability to a detergent or a chaotrope, the mutant membrane protein is incubated for a defined time in the presence of a test detergent or a test chaotropic agent and the stability is measured using for example ligand binding or a spectroscopic method as discussed above.

Suitable detergents for solubilisation of the membrane protein and/or mutant membrane protein and for measuring conformational stability are known to the skilled person in the art and include for example, dodecylmaltoside (DDM), CHAPS, octylglucoside (OG) and many others.

To determine increased stability to an extreme of pH, a typical pH test would be chosen, for example, in the range 4.5 to 5.5 (low pH) or in the range 8.5 to 9.5 (high pH).

In one embodiment the mutant transmembrane protein has increased conformational thermostability when compared to the parent membrane protein.

In another embodiment the mutant transmembrane protein has increased conformational thermostability compared to the parent membrane protein by at least 1° C.

According to a further aspect of the invention, there is provided a method of selecting a mutated transmembrane protein comprising the steps of;
   a) Providing one or more mutants of a parent transmembrane protein wherein the mutations are at the interfaces between transmembrane alpha-helices, or in a kinked region or in an alpha-helix adjacent to a kink.
   b) Contacting the mutated transmembrane protein with a ligand
   c) Determining the stability of the mutated transmembrane protein
   d) Identifying those mutants that exhibit increased conformational stability compared to the parent transmembrane protein.

Methods according to steps b) to d) are known in the art and described in WO2009/071914 incorporated herein by reference. It is appreciated that such methods are equally applicable to transmembrane transporters.

In one embodiment increased conformational stability is increased conformational thermostability.

In another embodiment increased conformational stability is determined in the presence of detergent.

Methods of providing one or more mutants of a parent transmembrane protein wherein the mutations are at the interfaces between transmembrane alpha-helices, or in a kinked region or in an alpha-helix adjacent to a kink is described above.

Methods of determining thermostability are as described in the methods section and in example 2.

In one embodiment the mutated parent transmembrane protein is contacted with a ligand prior to detergent-solubilisation and measurement of thermostability. Alternatively the mutated parent transmembrane protein is contacted with a ligand after detergent-solubilisation.

In one embodiment mutants of a parent transmembrane protein with increased conformational thermostability compared to the parent transmembrane protein were identified as having an increase in stability of at least 1° C.

According to a further aspect of the invention there is provided a method of producing a mutated transmembrane protein wherein the mutations are at the interfaces between transmembrane alpha-helices, or in a kinked region or in an alpha-helix adjacent to a kink, comprising carrying out the steps a) to d) and,
   e) Identifying the position of one or more of the mutated amino acid residues in those mutants that exhibit increased conformational stability, and
   Synthesising a mutant transmembrane protein which comprises the mutated residues identified in step e).

Methods for identifying the positions of the mutated amino acids according to step e) are carried out by sequencing techniques known in the art.

According to a further aspect of the invention there is provided a method of selecting a binding partner of a mutated transmembrane protein, the method comprising the steps of
   a) providing a mutant transmembrane protein which has increased conformational stability and/or is functionally inactive compared to its parent transmembrane protein, wherein the one or more mutations are located at the interfaces between transmembrane alpha-helices, or in a kinked region or in an alpha-helix adjacent to a kink.
   b) contacting the mutant transmembrane protein with one or more compounds
   c) determining whether the one or more compounds bind to the mutant transmembrane protein
   d) isolating one or more compounds.

The mutated transmembrane proteins which have been identified as having conformational stability have use in the identification of ligands which bind to the transmembrane protein when it is in a particular conformation. The provision of ligands which bind the transmembrane protein in a particular conformation are valuable tools for the development of agents for therapeutic use.

Methods of screening are known in the art and described in WO2008/004223 herein incorporated by reference. It is appreciated that such methods of screening are equally applicable to transmembrane transporters.

In one embodiment the mutant membrane protein is immobilised onto a solid support.

According to a further aspect of the invention there is provided a mutated transmembrane protein obtainable by the methods described herein.

Methods

All radiolabelled ligands were purchased from Perkin Elmer and detergents were from Anatrace.

Thermostability Assay

The thermostability of detergent-solubilised [$^{125}$I]-RTI55-bound SERT was determined as previously described for GPCRs (3, 4, 6, 7). Briefly, cells containing unpurified SERT were incubated with 1 nM [$^{125}$I]-RTI55 for 30 min on ice, which were then solubilised with detergent (DDM) on ice for 30 min before incubation at varying temperatures for 30 min. The radioligand bound to the membrane protein was separated from free radioligand by centrifugal gel filtration and the radioligand bound to the eluted transporter measured by liquid scintillation counting.

Radiolabelled Inhibitor Binding Assay

Saturation binding curves for membrane-bound SERT were obtained using a range of [$^{125}$I]-RTI55 concentrations from 0.13 nM to 160 nM in a 96-well plate format with non-specific binding being accounted for by incubating identical samples with 1 µM cocaine. The samples were incubated for 2 hours at 30° C. and then filtered on 96-well glass-fibre plates (Millipore) pre-treated with 200 µl 0.1% polyethyleneimine. The filters were washed three times with 200 µl ice-cold SERT buffer (100 mM NaCl, 20 mM Tris pH 7.4), dried for one hour at 50° C. prior to liquid scintillation counting. Competition binding assays were performed as above but a range of concentrations of unlabelled ligand was included and a final concentration of 0.2 nM [$^{125}$I]-RTI55 was used.

[$^3$H]-5HT Uptake Assays

The [$^3$H]-5HT uptake assays were performed with slight modifications to the method previously described (28). In brief, T-Rex293 cells and T-REx-SERT cells were plated onto poly-L-lysine-coated (1 mg/ml) 24-well plates, grown to 80% confluency, induced by the addition of 0.8 µg/ml tetracycline and grown for 48 hours. The growth medium was aspirated and the cells washed once with TB buffer (10 mM Hepes pH 7.5, 150 mM NaCl, 2 mM KCl, 1 mM CaCl$_2$, 1 mM MgCl$_2$). The assays were performed at 25° C. using 1 million cells in 400 µl TB buffer and 2 µM [$^3$H]-5HT and terminated 3 minutes after addition of substrate by three washes of ice-cold TB buffer containing 1 µM paroxetine or 10 µM cocaine. [$^3$H]-5HT was released by rupturing the cells with 2% SDS, which was quantified by liquid scintillation counting. Non-specific uptake was defined as [$^3$H]-5HT transport in the presence of 10 µM paroxetine or 10 µM cocaine.

EXAMPLES

Example 1: cDNA Expression of SERT in HEK293 Cells

Figures 1A, 1B:
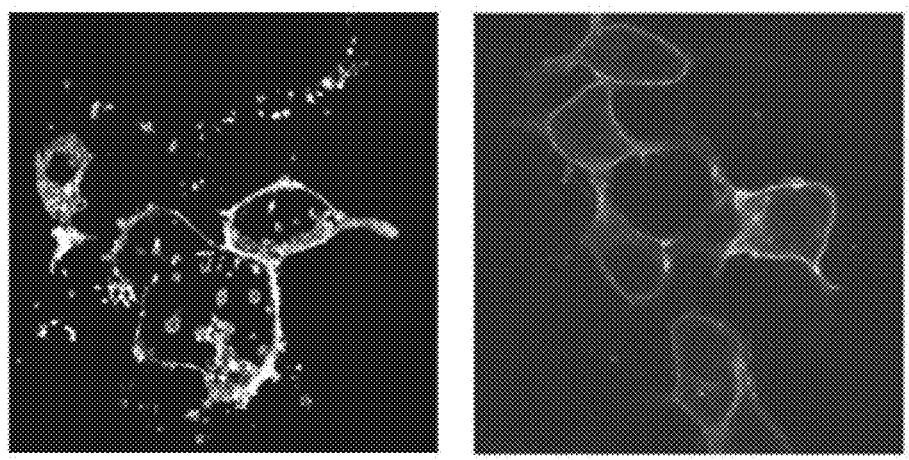
FIGS. 1A-1B Optimisation of SERT expression by transient transfection in T-Rex-HEK293 cells.

The construct C-myc-SERT-mCherry-BioHis10 was developed from the SERT cDNA in plasmid pCGT137 (23) and inserted into the mammalian cell expression vector pcDNA5/FRT/TO (Invitrogen), which was used for site directed mutagenesis and expression. Cells were induced for 48 hours with 1.2 µg/ml or 0.8 µg/ml tetracycline. 0.1-0.2 µg of plasmid per 50,000 T-Rex-HEK293 cells was identified as the optimal amount to ensure the majority of SERT was expressed at the cell surface as observed by confocal microscopy (FIG. 1A).

Stable cell lines expressing SAH6-GFP and SAH7-GFP in T-REx-293 cells were generated by selection with media containing 200 g/ml zeocin.

Example 2: Development of a Thermostability Assay for SERT

Figure 2A:
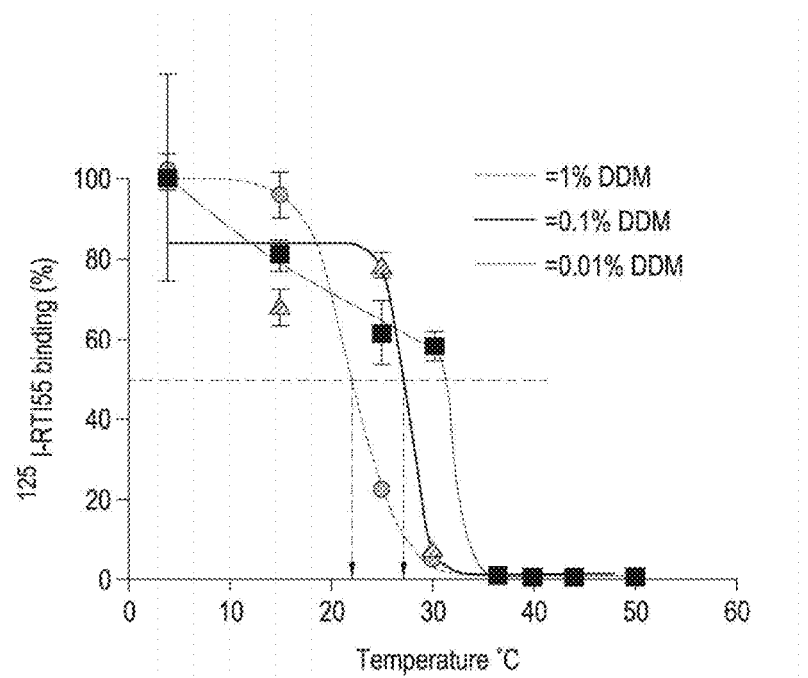
FIGS. 2A-2B Development of a thermostability assay for SERT.

Binding assays using an excess of [$^{125}$I]-RTI55 at a concentration of 1 nM (5 times the $K_D$) (23) showed that there were on average approximately 100,000 copies per transfected cell and that there were sufficient molecules of SERT in 50,000 cells per well of a 96-well plate to perform a single-point thermostability assay in duplicate. Thermostability was determined after solubilisation in three different concentrations of DDM (0.01%, 0.1% and 1%) (FIG. 2A).

Figure 2B:
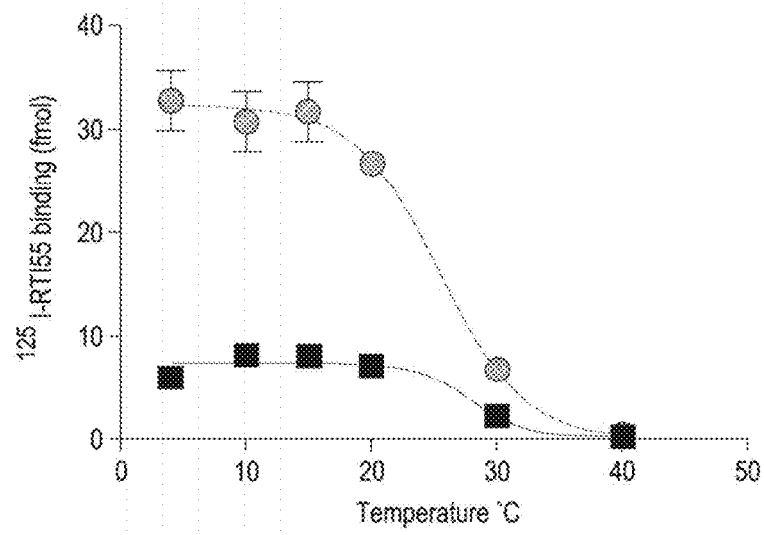

Thermostability assays usually involved adding the radioligand to detergent solubilised membrane proteins (7), but SERT is only stable in digitonin (29) therefore a different assay was developed where an inhibitor was used to stabilse the transporter. This entailed adding [$^{125}$I]-RTI55 to the T-Rex-HEK293 cells followed by detergent solubilisation and then the thermostability assay (heating samples at various temperatures for 30 minutes). The apparent $T_m$ was defined as the temperature where 50% of the transporter still bound the radiolabelled inhibitor (FIG. 2B). For [$^{125}$I]-RTI55-bound SERT, the apparent $T_m$ was 28° C., regardless of how it was expressed in HEK293 cells (FIG. 2B). Note that a considerable proportion of this thermostability is attributable to the bound inhibitor, because the apparent $T_m$ of DDM-solubilised SERT without bound [$^{125}$I]-RTI55 could not be measured. [$^{125}$I]-RTI55-bound SERT was also sensitive to the concentration of DDM present in the assays (FIGS. 2A-2B), with the apparent $T_m$ decreasing as the concentration of detergent increases. The most reproducible results with the steepest thermostability curve were obtained with a final concentration of 0.1% DDM, so this was used in subsequent assays to determine the thermostability of SERT mutants. The assays were repeated using either [$^3$H]-imipramine or [$^3$H]-paroxetine under identical conditions, but the binding characteristics of either ligand in the presence of DDM were unsatisfactory.

Example 3: Generation of SERT Mutants

Figure 3A:
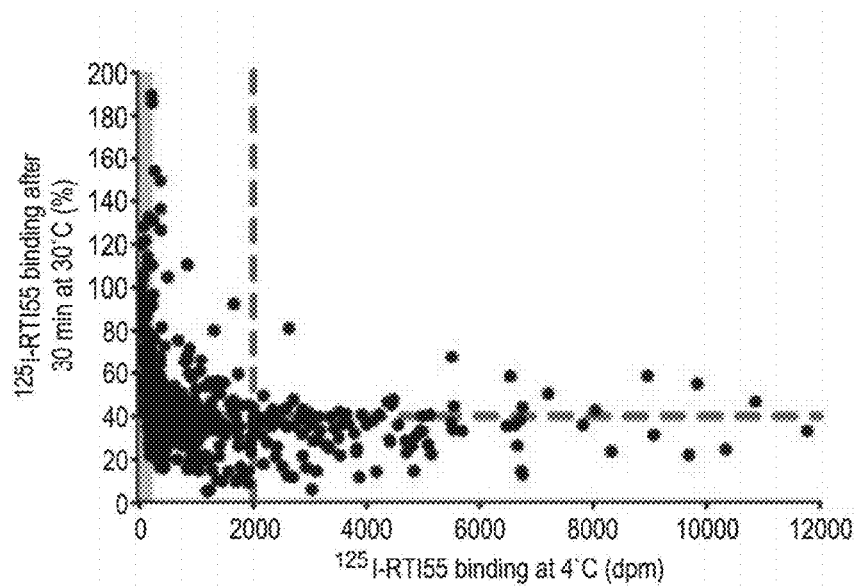
FIGS. 3A-3C Thermostabilisation of SERT (FIG. 3A) Comparison of [$^{125}$I]-RTI55 bound to 554 detergent-solubilised Ala/Leu mutants at either 4° C. or after heating at 30° C. for 30 minutes. The data relating to thermostability (the heated samples) have been normalized to the amount of wild-type SERT remaining after heating (40%; horizontal dashed line). The expression level of wild-type SERT is indicated by the vertical dashed line and the grey column (0-200 dpm) represents non-specific binding of [$^{125}$I]-RTI55 to the parental T-REx-HEK293 cell line (no SERT). Each data point represents binding to the equivalent of 50,000 cells measured in duplicate (estimated error is ±20% in dpm).
Figure 3B:
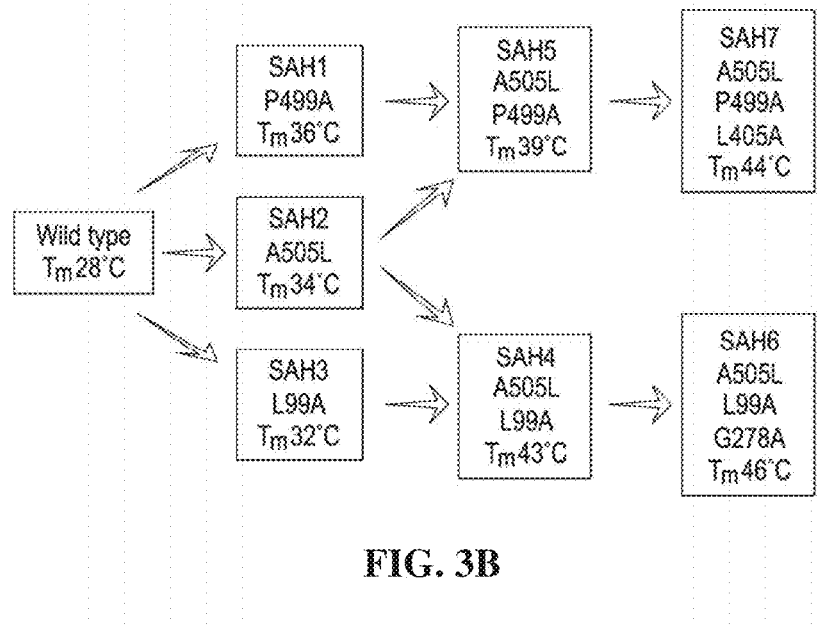
Figure 3C:
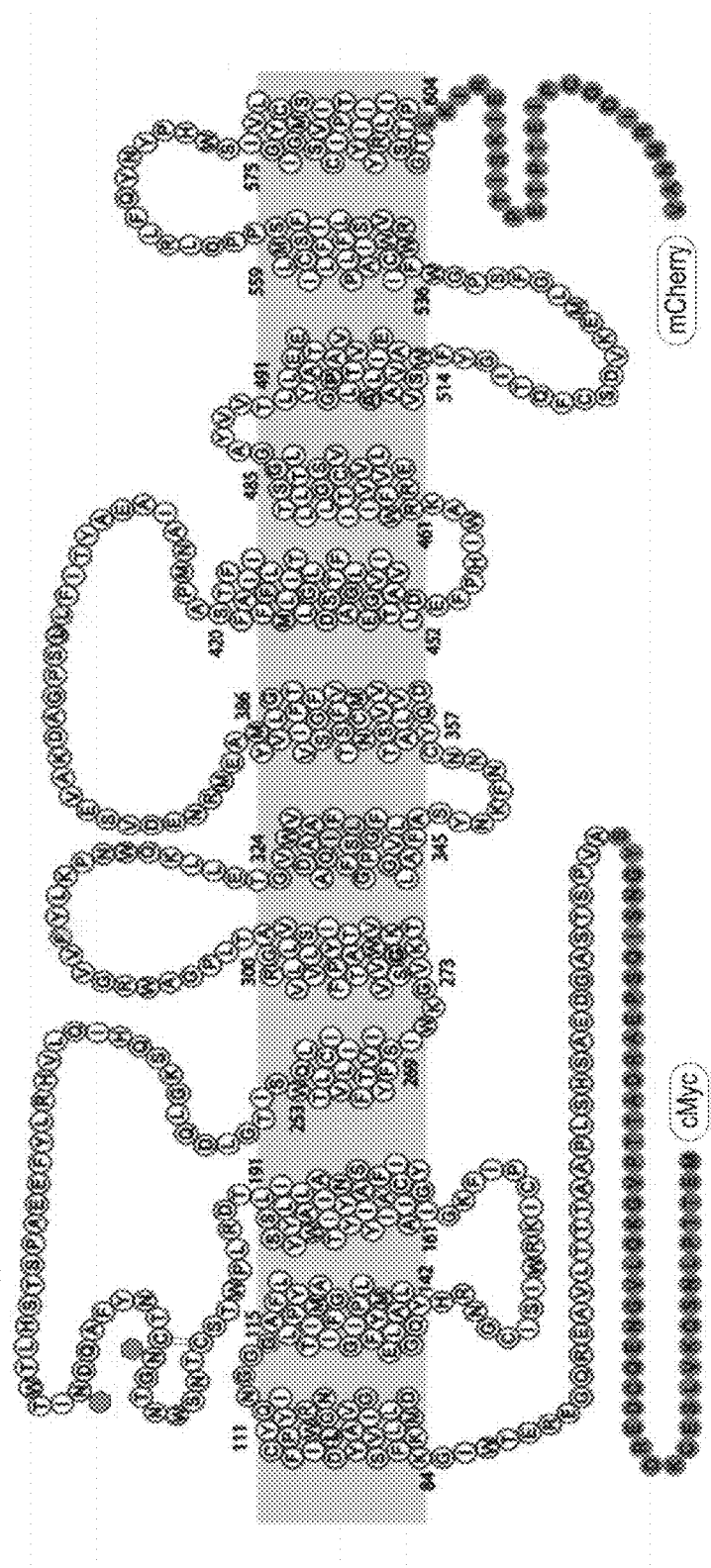

Systematic alanine-scanning mutagenesis was performed throughout SERT between amino residues 49 and 603, with each residue changed to alanine or, if the residue was already alanine, then it was changed to leucine. Mutants were generated by PCR using the QuikChange II methodology (Stratagene) using KOD Hot Start polymerase (Novagen). PCR reactions were transformed into XL1-competent cells (Stratagene). Mutations were combined by PCR as above, but using multiple primers. Each SERT-mCherry mutant was sequenced to ensure that only the desired mutation was present. A total of 554 mutants were constructed throughout the transmembrane domains and all loop regions (FIGS. 3A-3C).

The N-terminus and C-terminus were not mutated because these regions were predicted to be disordered and they are therefore unlikely to contribute to the thermostability of SERT. Plasmid DNA for each SERT-mCherry mutant was amplified using a Maxi-prep kit (Qiagen) and transiently transfected (GeneJuice, Novagen) into adherent mammalian T-REx-293 cells (50% confluent) grown in DMEM media supplemented with 10% tetracycline-free FBS and 5 µg/L blasticidin. Expression of mutants was induced by addition of 0.8 µg tetracycline/ml and incubation at 37° C. for 24 hours. Expression was assessed by fluorescence microscopy to ascertain whether the mutant was predominantly either at the plasma membrane or intracellular. The thermostability of each mutant was then determined using a single-temperature thermostability assay and compared to the thermostability of wild-type SERT. The sample was heated at 28° C. for 30 minutes and approximately 40% of wild-type SERT remained functional. Each batch of mutants tested contained wild-type SERT as a control so that the data between different experiments could be normalized (wild-type=40%). Analysis of the results (FIGS. 3A-3C) identified 34 mutations that appeared to improve the thermostability of SERT, but which did not decrease the levels of expression by more than 70%. Interestingly, there was no correlation between the levels of expression and thermostability of the mutants, in contrast to in GPCRs where a weak correlation was sometimes observed ($r^2$=0.2) (11). Of the 34 mutations identified, full thermostability curves showed that 10 mutations improved the thermostability of SERT by at least 1° C. as shown in Table 1 below.

TABLE 1

Thermostability and expression data for the most thermostable Ala/Leu mutants.

| Mutation | Expression (%) SERT = 100% | Cell surface expression | Apparent $T_m$ (° C.) | $\Delta T_m$ (° C.) |
|---|---|---|---|---|
| P499A | 65 | ** | 35 | 7 |
| A505L | 175 | *** | 34 | 6 |
| G113A | 42 | ** | 33 | 5 |
| L99A | 131 | ** | 32 | 4 |
| G278A | 39 | * | 31 | 3 |
| A169L | 31 | ** | 30 | 2 |
| F311A | 492 | ** | 30 | 2 |
| G115A | 327 | *** | 29 | 1 |
| L405A | 543 | *** | 29 | 1 |
| L406A | 87 | * | 29 | 1 |

The top 34 SERT mutants as estimated from the single point thermostability assay were re-tested using a 6-point thermostability curve to determine an accurate apparent $T_m$ and expressed as an improvement in $T_m$ ($\Delta T_m$) assuming wild-type SERT had an apparent $T_m$ of 28° C. Each mutant was also assessed for cell surface expression as determined by estimation by eye of fluorescence throughout the cell upon confocal microscopy: *, low expression;  as wild-type SERT, *, higher expression than wild-type SERT.

Figure 4:
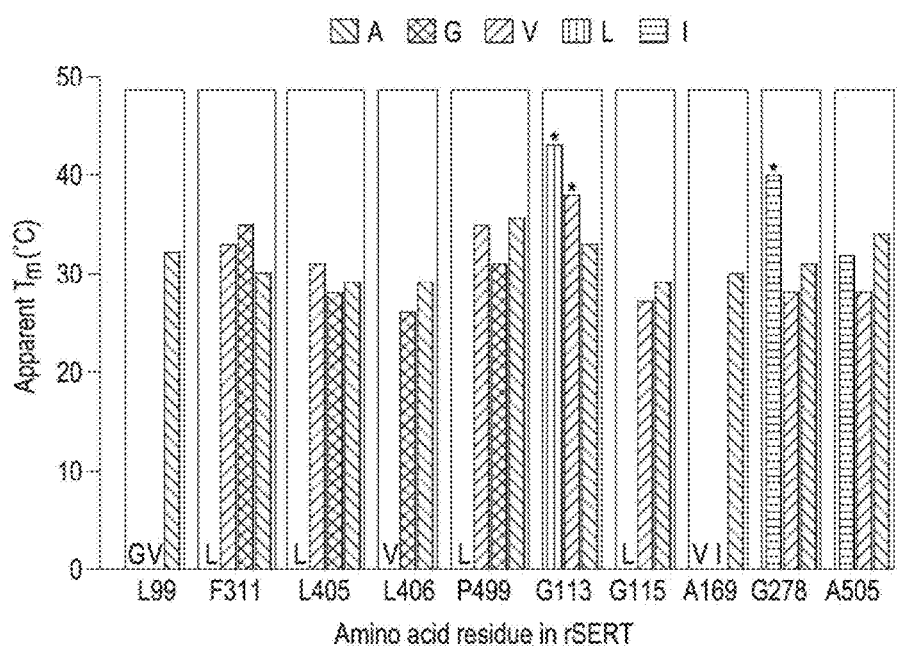
FIG. 4 Alternative amino acid residues for SERT thermostabilisation.

Of these 10 mutations, 7 were in the transmembrane helices and 3 in the extracellular loops (FIGS. 3A-3C). Further mutation of these Ala/Leu mutants to other amino acid residues did not significantly improve the thermostability of SERT (FIG. 4).

Combining the thermostabilising mutations in SERT was performed by a rational process previously described for the thermostabilisation of agonist-bound neurotensin receptor and adenosine $A_{2A}$ receptor (3). The best four thermostabilising mutations (P499A, A505L, L99A, G113A) were each combined with each other to make a series of double mutants (Table 2). Of these mutants, the most thermostable were A505L+L99A (SAH4) and A505L+P499A (SAH5). These double mutants were then combined with the remaining mutants to make triple mutants (Table 2), with the most thermostable being SAH6 (A505L+L99A+G278A) and SAH7 (A505L+P499A+L405A) with apparent $T_m$s 16° C. and 18° C. higher than wild-type SERT (FIGS. 5A-5B). Further combinations of mutations did not improve significantly the thermostability of these mutants (Table 2), so SAH6 and SAH7 were identified as the best candidates for structural studies and were therefore characterized further.

TABLE S2

Thermostability of double and triple mutants.

|  | SERT mutation | Apparent $T_m$ in 0.1% DDM |
|---|---|---|
| Wild type SERT | None | 28° C. |
| Double mutants | A505L + P499A (SAH5) | 39° C. |
|  | A505L + L99A (SAH4) | 43° C. |
|  | P499A + L99A | 35° C. |
|  | P499A + F311A | — |
|  | A505L + F311A | 32° C. |
|  | L99A + F311A | 27° C. |
| Triple mutants | A505L + P499A + L405A (SAH7) | 44° C. |
|  | A505L + P499A + A169L | 33° C. |
|  | A505L + P499A + F311A | 44° C. |
|  | A505L + P499A + L99A | — |
|  | A505L + L99A + G278A (SAH6) | 46° C. |
|  | A505L + L99A + F311A | 43° C. |
|  | A505L + L99A + L405A | 43° C. |
|  | A505L + L99A + L406A | 44° C. |
|  | A505L + L99A + N101A | 40° C. |
|  | A505L + L99A + G115A | 44° C. |
|  | A505L + F311A + L99A | 40° C. |
| Quadruple mutants | A505L + P499A + L405A + F311A | 44° C. |
|  | A505L + P499A + L405A + G115A | 45° C. |
|  | A505L + L99A + G278A + F311A | 44° C. |
|  | A505L + L99A + G278A + G115A | 44° C. |
|  | A505L + L99A + G278A + L405A | 44° C. |

Combinations of SERT mutants tested for the thermostabilisation of $^{125}$I-RTI55-bound detergent-solubilised SERT (apparent $T_m \pm 1°$ C.).

Surprisingly, when the mutations were mapped to the LeuT structure, all the mutations in SAH6 and SAH7 are found at the interfaces between transmembrane α-helices and, more specifically, in either a kinked region or in an α-helix adjacent to a kink. The conserved nature of amino acid residues that have been mutated to improve thermostability of SERT suggests that similar mutations in related transporters such as for norepinephrine (NET) and dopamine (DAT) would also improve their thermostability, as has been observed when thermostabilising mutations have been transferred between closely related GPCRs (37).

Example 4: Characterisation of Optimally Stabilised Mutants SAH6 and SAH7

Radioligand binding assays were performed on the thermostabilised SERT mutants as described above. The affinity of SAH6 and SAH7 for [$^{125}$I]-RTI55 in saturation ligand binding assays was found to be largely unchanged with apparent $K_D$s of 3.8±0.1 nM and 1.3±0.1 nM, respectively, compared to 1.6 nM±0.1 nM for wild-type SERT (FIGS. 7A-7C). Competition binding assays (FIGS. 7A-7C) showed that SAH6 had an apparent affinity for cocaine 17-fold higher than wild-type SERT (FIG. 6), whilst there was a small decrease in affinity for ibogaine, imipramine, paroxetine and serotonin (4.5-, 6.7-, 90-, 2.9-fold, respectively). SAH7 showed a similar profile of binding, although the absolute values differed slightly (FIGS. 7A-7C, FIG. 6).

Both SAH6 and SAH7 were found to be more stable in short chain detergents that are suitable for crystallography (11) and hence possess the most valuable and useful characteristic of thermostabilised GPCRs. SAH6 and SAH7 were also more tolerant to short chain detergents than wild type SERT (FIGS. 5A-5B).

The affinity of [$^{125}$I]-RTI55 for both SAH6 and SAH7 is virtually identical to the wild-type transporter (23), which strongly supports the contention that the mutants are folded in a biologically relevant conformation. This is further supported by the cell surface expression of both mutants in stable cell lines expressing either SAH6 or SAH7, as misfolded SERT is retained in the endoplasmic reticulum (ER). Competition assays using both inhibitors and the substrate 5-HT provide further evidence on the likely conformation that has been stabilised. Both SAH6 and SAH7 bind cocaine with higher affinity than wild-type SERT. None of the mutations are in the region proposed to be the inhibitor binding site (30, 31) so in analogy to what has been previously observed in GPCRs, these data suggest that SAH6 and SAH7 have been stabilised in a 'cocaine-bound' conformation. As cocaine has been proposed to bind preferentially to the outward-open conformation of SERT (32), it is likely that both SAH6 and SAH7 are thermostabilised in an outward-open state. The decrease in binding affinity of both imipramine and paroxetine for SAH6 is consistent with this interpretation, as there are likely to be subtle differences between the binding of these inhibitors compared to RTI55, even though they are all proposed to bind to the outward-open state (33, 34).

Example 5: Functional Activity of SAH6 and SAH7 Mutants

A characteristic of transporters is obviously their ability to facilitate the vectorial movement of substrates across biological membranes. 5HT transport catalysed by SAH6 and SAH7 was therefore compared with the wild-type transporter in stable cell lines that robustly express the transporters on the cell surface of a tetracycline-inducible HEK293 cell line (35, 36).

Although both SAH6 and SAH7 were capable of binding inhibitors and the substrate serotonin, no significant transport of [$^3$H]-5HT into the cell was observed in cell lines expressing cell surface-expressed SAH6 or SAH7, despite the presence of the mutants in the plasma membrane as defined by confocal microscopy (FIGS. 8A-8B) suggesting that the receptors are preferentially in one particular conformation. This is not due to alterations in the binding site for 5HT, because 5HT prevented [$^{125}$I]-RTI55 binding in competition assays although the affinity for 5HT was decreased by 1.5-2.9 fold. These data are consistent with the theory that both SAH6 and SAH7 are thermostabilised in a specific outward-open conformation.

Example 6: Mapping of Thermostabilising Mutations to LeuT

There is a growing body of data which suggests that the structure of SERT is very similar to that of the bacterial transporter LeuT. Structures of LeuT bound to antidepressant drugs have been determined, where the antidepressant drugs are also known to bind SERT (30, 31) and despite the large difference in binding affinities (nM compared to nM), has led to plausible models for how antidepressant drugs inhibit SERT. We have therefore mapped the thermostabilising mutations identified herein to the structure of LeuT bound to sertraline (FIGS. 9-11C, FIG. 12A-12D). Surprisingly it was found that all the mutations in SAH6 and SAH7 are found at the interfaces between transmembrane α-helices and. More specifically, in either a kinked region or in an α-helix adjacent to a kink. This suggests that mutations in specific regions of a protein can be applied across a range of membrane proteins having similar three-dimensional structures, thereby improving the probability of obtaining conformationally stable mutants for use in crystallisation.

Example 7: Expression and Crystallisation of Thermostabilised SERT

A stable HEK293-GnTI⁻ cell line was constructed that expressed the thermostabilised serotonin transporter (SERT) to high levels. On induction with tetracycline, thermostabilised SERT was expressed sufficiently to allow the purification of 2 mg of transporter from 10 L of cells using the detergent dodecylmaltoside. Crystals were produced by vapour diffusion methodology in 23% PEG400, 100 mM MES pH 5.9 and they diffracted isotropically to about 8 Å resolution.

REFERENCES

1. Rosenbaum, D. M., (2007) Science. 318 (5854):1266-1273
2. Cherezov, V. (2007) Science, 318 (5854):1258-1265
3. Lebon, G., Bennett, K., Jazayeri, A. & Tate, C. G. (2011). *J Mol Biol* 409, 298-310;
4. Magnani, F., Shibata, Y., Serrano-Vega, M. J. & Tate, C. G. (2008). *Proc Natl Acad Sci USA* 105, 10744-10749;
5. Miller, J. L. & Tate, C. G. (2011). *J Mol Biol* 413, 628-638;
6. Serrano-Vega, M. J., Magnani, F., Shibata, Y. & Tate, C. G. (2008). *Proc Natl Acad Sci USA* 105, 877-882;
7. Shibata, Y., White, J. F., Serrano-Vega, M. J., Magnani, F., Aloia, A. L., Grisshammer, R. & Tate, C. G. (2009). *J Mol Biol* 390, 262-277.
8. Hino, T., Arakawa, T., Iwanari, H., Yurugi-Kobayashi, T., Ikeda-Suno, C., Nakada-Nakura, Y., Kusano-Arai, O., Weyand, S., Shimamura, T., Nomura, N., Cameron, A. D., Kobayashi, T., Hamakubo, T., Iwata, S. & Murata, T. (2012). *Nature* 482, 237-240
9. Rasmussen, S. G., Choi, H. J., Fung, J. J., Pardon, E., Casarosa, P., Chae, P. S., Devree, B. T., Rosenbaum, D. M., Thian, F. S., Kobilka, T. S., Schnapp, A., Konetzki, I., Sunahara, R. K., Gellman, S. H., Pautsch, A., Steyaert, J., Weis, W. I. & Kobilka, B. K. (2011). *Nature* 469, 175-180.
10. Rasmussen, S. G., Choi, H. J., Rosenbaum, D. M., Kobilka, T. S., Thian, F. S., Edwards, P. C., Burghammer, M., Ratnala, V. R., Sanishvili, R., Fischetti, R. F., Schertler, G. F., Weis, W. I. & Kobilka, B. K. (2007). *Nature* 450, 383-387
11. Tate, C. G. (2012). *Trends Biochem Sci* 37, 343-352; Tate, C. G. (2010). *Methods Mol Biol* 601, 187-203.
12. Lebon, G., Warne, T., Edwards, P. C., Bennett, K., Langmead, C. J., Leslie, A. G. & Tate, C. G. (2011). *Nature* 474, 521-525.
13. Warne, T., Moukhametzianov, R., Baker, J. G., Nehme, R., Edwards, P. C., Leslie, A. G., Schertler, G. F. & Tate, C. G. (2011). *Nature* 469, 241-244.
14. S. H White (2004) *Protein Sci* 13, 1948-1949.
15. C. G. Tate (2001) *FEBS Lett* 504, 94-98.
16. R. Grisshammer, C. G. Tate (1995) *Q Rev Biophys* 28, 315-422.
17. Hahn, M. K. & Blakely, R. D. (2007) *Annu Rev Pharmacol Toxicol* 47, 401-441
18. Kristensen, A. S., Andersen, J., Jorgensen, T. N., Sorensen, L., Eriksen, J., Loland, C. J., Stromgaard, K. & Gether, U. (2011). *Pharmacol Rev* 63, 585-640.
19. Bill, R. M., Henderson, P. J., Iwata, S., Kunji, E. R., Michel, H., Neutze, R., Newstead, S., Poolman, B., Tate, C. G. & Vogel, H. (2011) *Nat Biotechnol* 29, 335-340).
20. Vinothkumar, K. R. & Henderson, R. (2010). *Q Rev Biophys* 43, 65-158.
21. Tate, C. G. (1998) Methods Enzymol 296, 443-455;
22. Tate, C. G. & Blakely, R. D. (1994) J Biol Chem 269, 26303-26310.
23. Tate, C. G. & Blakely, R. D. (1994). The effect of N-linked glycosylation on activity of the Na(+)- and Cl(−)-dependent serotonin transporter expressed using recombinant baculovirus in insect cells. J Biol Chem 269, 26303-26310.
24. Tate, C. G., Whiteley, E. & Betenbaugh, M. J. (1999) *J Biol Chem* 274, 17551-17558.
25. Broer, S. & Gether, U. (2012) *Br J Pharmacol* 167, 256-278.
26. Yamashita, A., Singh, S. K., Kawate, T., Jin, Y. & Gouaux, E. (2005) *Nature* 437, 215-223.
27. Scanlon, S. M., Williams, D. C. & Schloss, P. (2001) Biochemistry 40, 10507-10513.
28. Magnani, F., Tate, C. G., Wynne, S., Williams, C. & Haase, J. (2004). Partitioning of the serotonin transporter into lipid microdomains modulates transport of serotonin. J Biol Chem 279, 38770-38778.
29. Talvenheimo, J. & Rudnick, G. (1980) J Biol Chem 255, 8606-8611.
30. Singh, S. K., Yamashita, A. & Gouaux, E. (2007). Antidepressant binding site in a bacterial homologue of neurotransmitter transporters. *Nature* 448, 952-956.
31. Zhou, Z., Zhen, J., Karpowich, N. K., Law, C. J., Reith, M. E. & Wang, D. N. (2009). Antidepressant specificity of serotonin transporter suggested by three LeuT-SSRI structures. Nat Struct Mol Biol 16, 652-657.
32. Rasmussen, S. G., Carroll, F. I., Maresch, M. J., Jensen, A. D., Tate, C. G. & Gether, U. (2001). Biophysical characterization of the cocaine binding pocket in the serotonin transporter using a fluorescent cocaine analogue as a molecular reporter. J Biol Chem 276, 4717-4723.
33. Sarker, S., Weissensteiner, R., Steiner, I., Sitte, H. H., Ecker, G. F., Freissmuth, M. & Sucic, S. (2010). The high-affinity binding site for tricyclic antidepressants resides in the outer vestibule of the serotonin transporter. Mol Pharmacol 78, 1026-1035.
34. Schloss, P. & Betz, H. (1995). Heterogeneity of antidepressant binding sites on the recombinant rat serotonin transporter SERT1. Biochemistry 34, 12590-12595.
35. Tate, C. G., Haase, J., Baker, C., Boorsma, M., Magnani, F., Vallis, Y. & Williams, D. C. (2003). Comparison of seven different heterologous protein expression systems for the production of the serotonin transporter. Biochim Biophys Acta 1610, 141-153.

36. Magnani, F., Tate, C. G., Wynne, S., Williams, C. & Haase, J. (2004). Partitioning of the serotonin transporter into lipid microdomains modulates transport of serotonin. J Biol Chem 279, 38770-38778.
37. Serrano-Vega, M. J. & Tate, C. G. (2009). Transferability of thermostabilizing mutations between beta-adrenergic receptors. *Mol Membr Biol* 26, 385-396.
38. Smirnova, I. N., Kaback, R. H., (2003), *Biochemistry* 42, 3025-3031
39. Abramson, J., Smirnova, I., Kasho, V., Verner, G., Kaback, R. H., Iwata, S., (2003) *Science*, 301, 610-615.
40. Jardetzky O (1966), *Nature*, 211 (5052): 969-970.
41. Shimamura, T. et al. (2010), Science 328 (5977):470-473

---

The invention claimed is:

1. A mutant membrane protein which has increased conformational stability compared to its parent membrane protein, wherein the one or more mutations are located at the interfaces between transmembrane alpha-helices, or in a kinked region or in an alpha-helix adjacent to a kink, wherein the mutant membrane protein is the cocaine-sensitive rat serotonin transporter (SERT) protein which comprises one or more amino acid mutations selected from P499A, A505L, G113A, L99A, G278A, A169L, F311A, G115A, L405A and L406A.

2. The mutant membrane protein according to claim 1 comprising three mutations selected from G278A, A505L, L99A and P499A.

3. The mutant membrane protein according to claim 1 comprising mutations L99A, G278A and A505L.

4. The mutant membrane protein according to claim 1 comprising mutations L405A, P499A and A505L.

5. The mutant membrane protein according to claim 1 which is bound to a ligand.

6. A method of selecting a binding partner of a mutated membrane protein, the method comprising the steps of
   a) providing a mutant membrane protein according to claim 1,
   b) contacting the mutant membrane protein with one or more compounds,
   c) determining whether the one or more compounds bind to the mutant membrane protein, and
   d) isolating one or more compounds.

7. The method according to claim 6 wherein mutant membrane protein is immobilised onto a solid support.

8. A mutant membrane protein which has increased conformational stability compared to its parent membrane protein, wherein the one or more mutations are located at the interfaces between transmembrane alpha-helices, or in a kinked region or in an alpha-helix adjacent to a kink, comprising at least one or more mutations which are at the corresponding amino acid positions of P499A, A505L, G113A, L99A, G278A, A169L, F311A, G115A, L405A and L406A of SEQ ID NO: 1.

* * * * *

SEQUENCE LISTING

```
<160> NUMBER OF SEQ ID NOS: 2

<210> SEQ ID NO 1
<211> LENGTH: 630
<212> TYPE: PRT
<213> ORGANISM: Rattus sp.

<400> SEQUENCE: 1

Met Glu Thr Thr Pro Leu Asn Ser Gln Lys Val Leu Ser Glu Cys Lys
1               5                   10                  15

Asp Arg Glu Asp Cys Gln Glu Asn Gly Val Leu Gln Lys Gly Val Pro
            20                  25                  30

Thr Thr Ala Asp Arg Ala Glu Pro Ser Gln Ile Ser Asn Gly Tyr Ser
        35                  40                  45

Ala Val Pro Ser Thr Ser Ala Gly Asp Glu Ala Ser His Ser Ile Pro
    50                  55                  60

Ala Ala Thr Thr Thr Leu Val Ala Glu Ile Arg Gln Gly Glu Arg Glu
65                  70                  75                  80

Thr Trp Gly Lys Lys Met Asp Phe Leu Leu Ser Val Ile Gly Tyr Ala
                85                  90                  95

Val Asp Leu Gly Asn Ile Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Ile Ala Ser Tyr Tyr
                165                 170                 175

Asn Thr Ile Ile Ala Trp Ala Leu Tyr Tyr Leu Ile Ser Ser Leu Thr
            180                 185                 190

Asp Arg Leu Pro Trp Thr Ser Cys Thr Asn Ser Trp Asn Thr Gly Asn
        195                 200                 205

Cys Thr Asn Tyr Phe Ala Gln Asp Asn Ile Thr Trp Thr Leu His Ser
    210                 215                 220

Thr Ser Pro Ala Glu Glu Phe Tyr Leu Arg His Val Leu Gln Ile His
225                 230                 235                 240

Gln Ser Lys Gly Leu Gln Asp Leu Gly Thr Ile Ser Trp Gln Leu Thr
                245                 250                 255

Leu Cys Ile Val Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Val Leu Ser Val Leu Leu Val Arg Gly Ala Thr Leu Pro Gly
    290                 295                 300

Ala Trp Arg Gly Val Val Phe Tyr Leu Lys Pro Asn Trp Gln Lys Leu
305                 310                 315                 320
```

-continued

Leu Glu Thr Gly Val Trp Val Asp Ala Ala Ala Gln Ile Phe Phe Ser
            325                 330                 335

Leu Gly Pro Gly Phe Gly Val Leu Leu Ala Phe Ala Ser Tyr Asn Lys
        340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
                420                 425                 430

Thr Leu Gly Leu Asp Ser Thr Phe Ala Gly Leu Glu Gly Val Ile Thr
            435                 440                 445

Ala Val Leu Asp Glu Phe Pro His Ile Trp Ala Lys Arg Arg Glu Trp
    450                 455                 460

Phe Val Leu Ile Val Ile Thr Cys Val Leu Gly Ser Leu Leu Thr
465                 470                 475                 480

Leu Thr Ser Gly Gly Ala Tyr Val Val Thr Leu Leu Glu Glu Tyr Ala
                485                 490                 495

Thr Gly Pro Ala Val Leu Thr Val Ala Leu Ile Glu Ala Val Ala Val
                500                 505                 510

Ser Trp Phe Tyr Gly Ile Thr Gln Phe Cys Ser Asp Val Lys Glu Met
        515                 520                 525

Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro His Trp Ser Ile Val
                565                 570                 575

Leu Gly Tyr Cys Ile Gly Met Ser Ser Val Ile Cys Ile Pro Thr Tyr
            580                 585                 590

Ile Ile Tyr Arg Leu Ile Ser Thr Pro Gly Thr Leu Lys Glu Arg Ile
        595                 600                 605

Ile Lys Ser Ile Thr Pro Glu Thr Pro Thr Glu Ile Pro Cys Gly Asp
    610                 615                 620

Ile Arg Met Asn Ala Val
625                 630

<210> SEQ ID NO 2
<211> LENGTH: 519
<212> TYPE: PRT
<213> ORGANISM: Aquifex

<400> SEQUENCE: 2

Met Glu Val Lys Arg Glu His Trp Ala Thr Arg Leu Gly Leu Ile Leu
1               5                   10                  15

Ala Met Ala Gly Asn Ala Val Gly Leu Gly Asn Phe Leu Arg Phe Pro
            20                  25                  30

Val Gln Ala Ala Glu Asn Gly Gly Ala Phe Met Ile Pro Tyr Ile
        35                  40                  45

Ile Ala Phe Leu Leu Val Gly Ile Pro Leu Met Trp Ile Glu Trp Ala
    50                  55                  60

```
Met Gly Arg Tyr Gly Gly Ala Gln Gly His Gly Thr Thr Pro Ala Ile
 65                  70                  75                  80

Phe Tyr Leu Leu Trp Arg Asn Arg Phe Ala Lys Ile Leu Gly Val Phe
                 85                  90                  95

Gly Leu Trp Ile Pro Leu Val Val Ala Ile Tyr Tyr Val Tyr Ile Glu
                100                 105                 110

Ser Trp Thr Leu Gly Phe Ala Ile Lys Phe Leu Val Gly Leu Val Pro
            115                 120                 125

Glu Pro Pro Asn Ala Thr Asp Pro Asp Ser Ile Leu Arg Pro Phe
            130                 135                 140

Lys Glu Phe Leu Tyr Ser Tyr Ile Gly Val Pro Lys Gly Asp Glu Pro
145                 150                 155                 160

Ile Leu Lys Pro Ser Leu Phe Ala Tyr Ile Val Phe Leu Ile Thr Met
                165                 170                 175

Phe Ile Asn Val Ser Ile Leu Ile Arg Gly Ile Ser Lys Gly Ile Glu
                180                 185                 190

Arg Phe Ala Lys Ile Ala Met Pro Thr Leu Phe Ile Leu Ala Val Phe
            195                 200                 205

Leu Val Ile Arg Val Phe Leu Leu Glu Thr Pro Asn Gly Thr Ala Ala
210                 215                 220

Asp Gly Leu Asn Phe Leu Trp Thr Pro Asp Phe Glu Lys Leu Lys Asp
225                 230                 235                 240

Pro Gly Val Trp Ile Ala Ala Val Gly Gln Ile Phe Phe Thr Leu Ser
                245                 250                 255

Leu Gly Phe Gly Ala Ile Ile Thr Tyr Ala Ser Tyr Val Arg Lys Asp
            260                 265                 270

Gln Asp Ile Val Leu Ser Gly Leu Thr Ala Ala Thr Leu Asn Glu Lys
            275                 280                 285

Ala Glu Val Ile Leu Gly Gly Ser Ile Ser Ile Pro Ala Ala Val Ala
            290                 295                 300

Phe Phe Gly Val Ala Asn Ala Val Ala Ile Ala Lys Ala Gly Ala Phe
305                 310                 315                 320

Asn Leu Gly Phe Ile Thr Leu Pro Ala Ile Phe Ser Gln Thr Ala Gly
                325                 330                 335

Gly Thr Phe Leu Gly Phe Leu Trp Phe Phe Leu Leu Phe Phe Ala Gly
            340                 345                 350

Leu Thr Ser Ser Ile Ala Ile Met Gln Pro Met Ile Ala Phe Leu Glu
            355                 360                 365

Asp Glu Leu Lys Leu Ser Arg Lys His Ala Val Leu Trp Thr Ala Ala
            370                 375                 380

Ile Val Phe Phe Ser Ala His Leu Val Met Phe Leu Asn Lys Ser Leu
385                 390                 395                 400

Asp Glu Met Asp Phe Trp Ala Gly Thr Ile Gly Val Val Phe Phe Gly
            405                 410                 415

Leu Thr Glu Leu Ile Ile Phe Phe Trp Ile Phe Gly Ala Asp Lys Ala
            420                 425                 430

Trp Glu Glu Ile Asn Arg Gly Gly Ile Ile Lys Val Pro Arg Ile Tyr
            435                 440                 445

Tyr Tyr Val Met Arg Tyr Ile Thr Pro Ala Phe Leu Ala Val Leu Leu
            450                 455                 460

Val Val Trp Ala Arg Glu Tyr Ile Pro Lys Ile Met Glu Glu Thr His
465                 470                 475                 480
```

```
Trp Thr Val Trp Ile Thr Arg Phe Tyr Ile Ile Gly Leu Phe Leu Phe
                485                 490                 495

Leu Thr Phe Leu Val Phe Leu Ala Glu Arg Arg Arg Asn His Glu Ser
            500                 505                 510

Ala Gly Thr Leu Val Pro Arg
            515
```